(12) United States Patent  (10) Patent No.: US 8,790,409 B2
Van den Heuvel et al.  (45) Date of Patent: Jul. 29, 2014

(54) SECURABLE IMPLANTABLE COMPONENT

(71) Applicants: Koen Van den Heuvel, Macquarie Park (AU); Joris Walraevens, Macquarie Park (AU); Wim Bervoets, Macquarie Park (AU)

(72) Inventors: Koen Van den Heuvel, Macquarie Park (AU); Joris Walraevens, Macquarie Park (AU); Wim Bervoets, Macquarie Park (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/707,764

(22) Filed: Dec. 7, 2012

(65) Prior Publication Data

US 2014/0163692 A1  Jun. 12, 2014

(51) Int. Cl.
*A61F 2/28* (2006.01)
*A61F 2/30* (2006.01)

(52) U.S. Cl.
USPC ............... 623/18.12; 623/16.11; 623/18.11

(58) Field of Classification Search
CPC .................................. A61F 2/28; A61F 2/2875
USPC ............ 623/11.11, 16.11, 17.18–18.12
See application file for complete search history.

(56) References Cited

PUBLICATIONS

SerenoCem™, "Ionomeric Bone Cement and Granules, The Bioactive Material designed specifically for use in the middle ear," retrieved from www.shreyaas.net/Pdf/sernocem_literature.pdf, on Dec. 7, 2012.
Tysome, et al., "How we do it: ionomeric cement to attach the stapes prosthesis to the long process of the incus," Clinical Otolaryngology, 30, pp. 458-460, Jan. 31, 2005.
SerenoCem Bibliography, Applications of glass-ionomer cements, retrieved from http://www.corinthiansurgical.com/products/serenocem-cement, on Dec. 7, 2012.

*Primary Examiner* — Jason-Dennis Stewart
(74) *Attorney, Agent, or Firm* — Edell, Shapiro & Finnan, LLC

(57) ABSTRACT

Implantable components configured to be secured to a recipient with a bonding agent are presented herein. The implantable components are configured to be implanted adjacent to a recipient's bone and/or tissue and have a surface for attachment to the bonding agent.

17 Claims, 24 Drawing Sheets

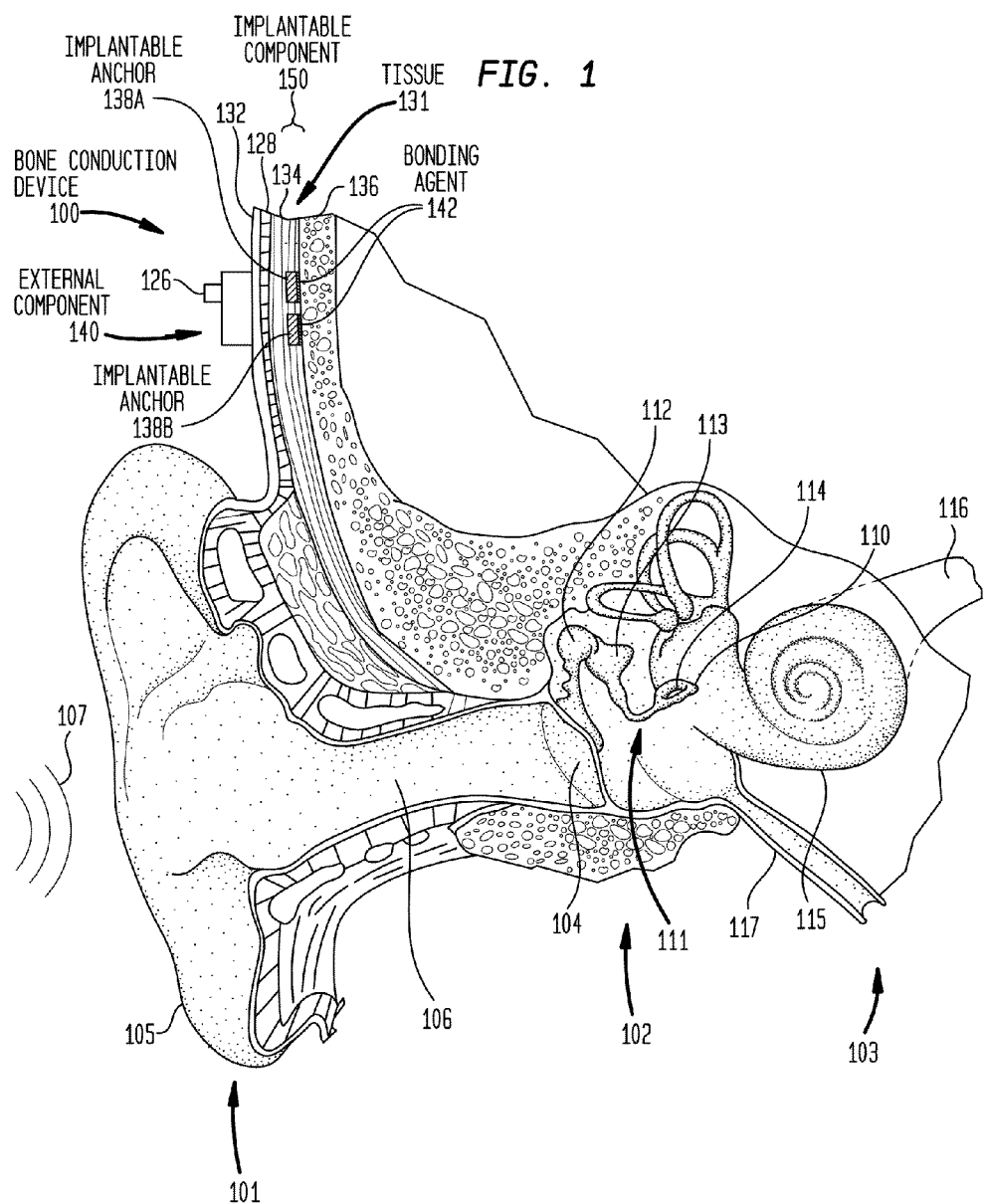

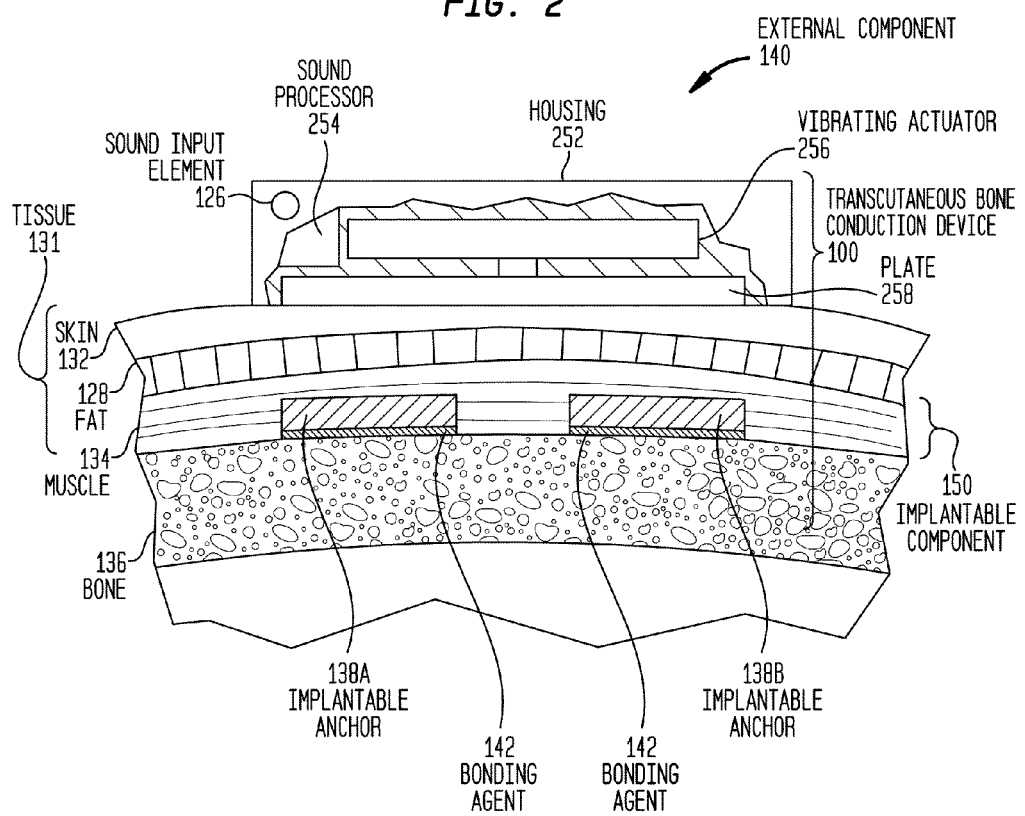

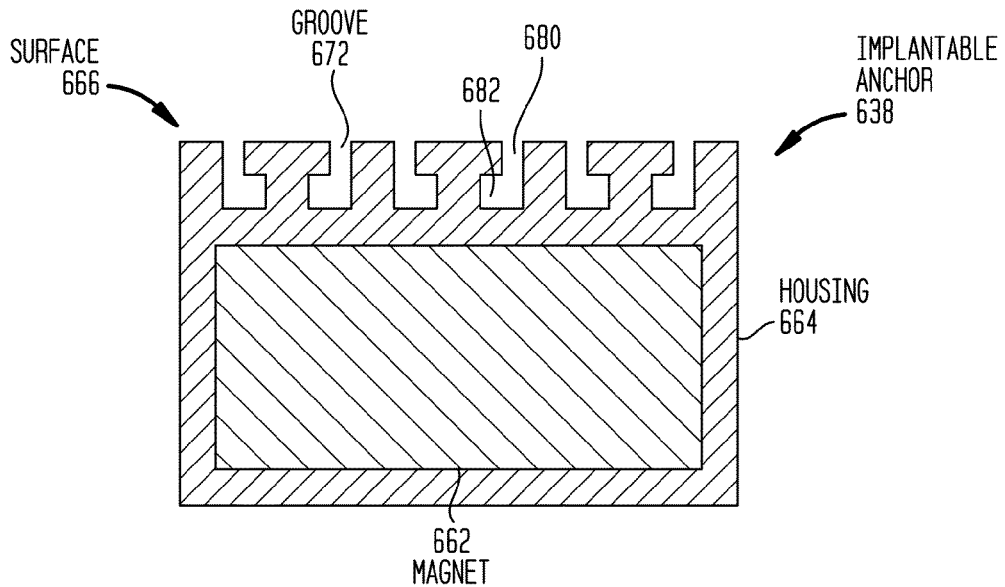
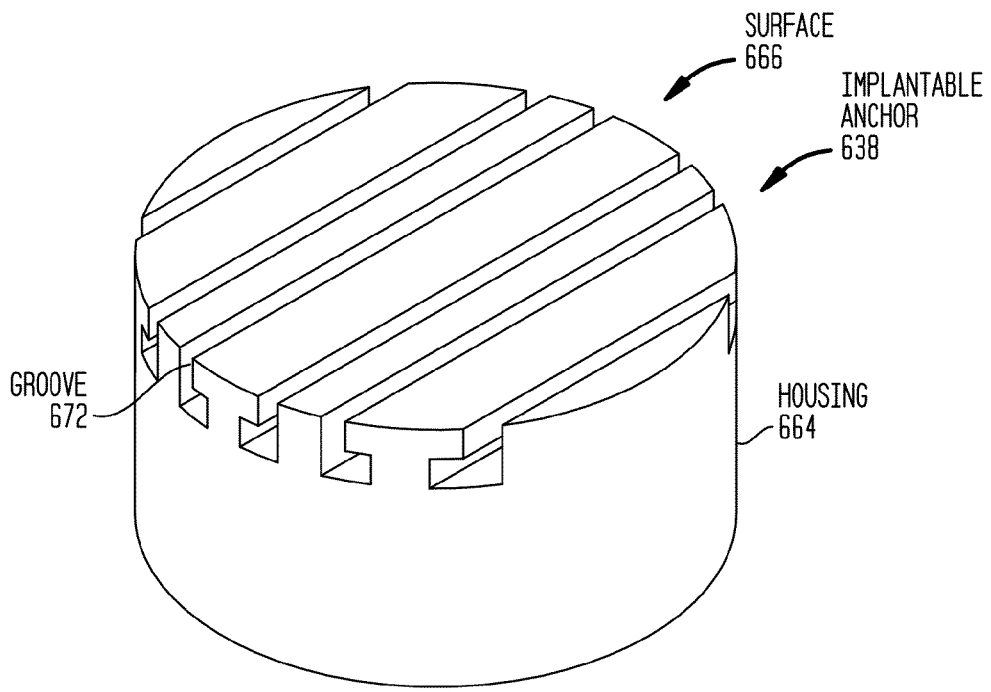

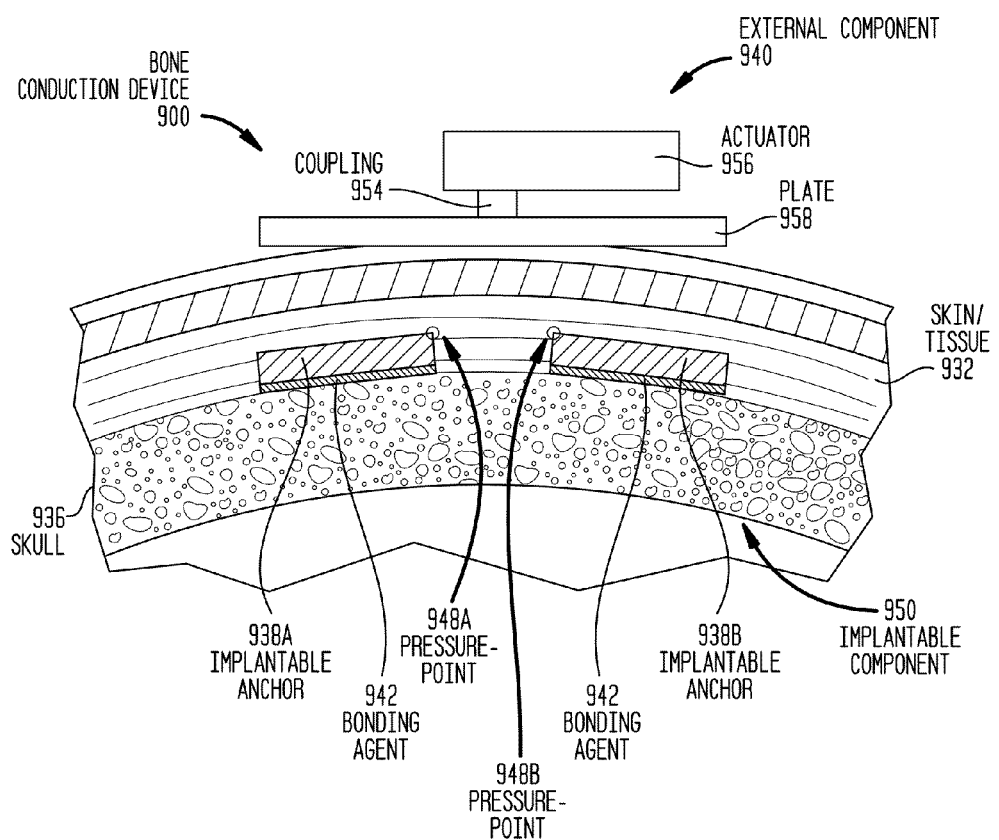

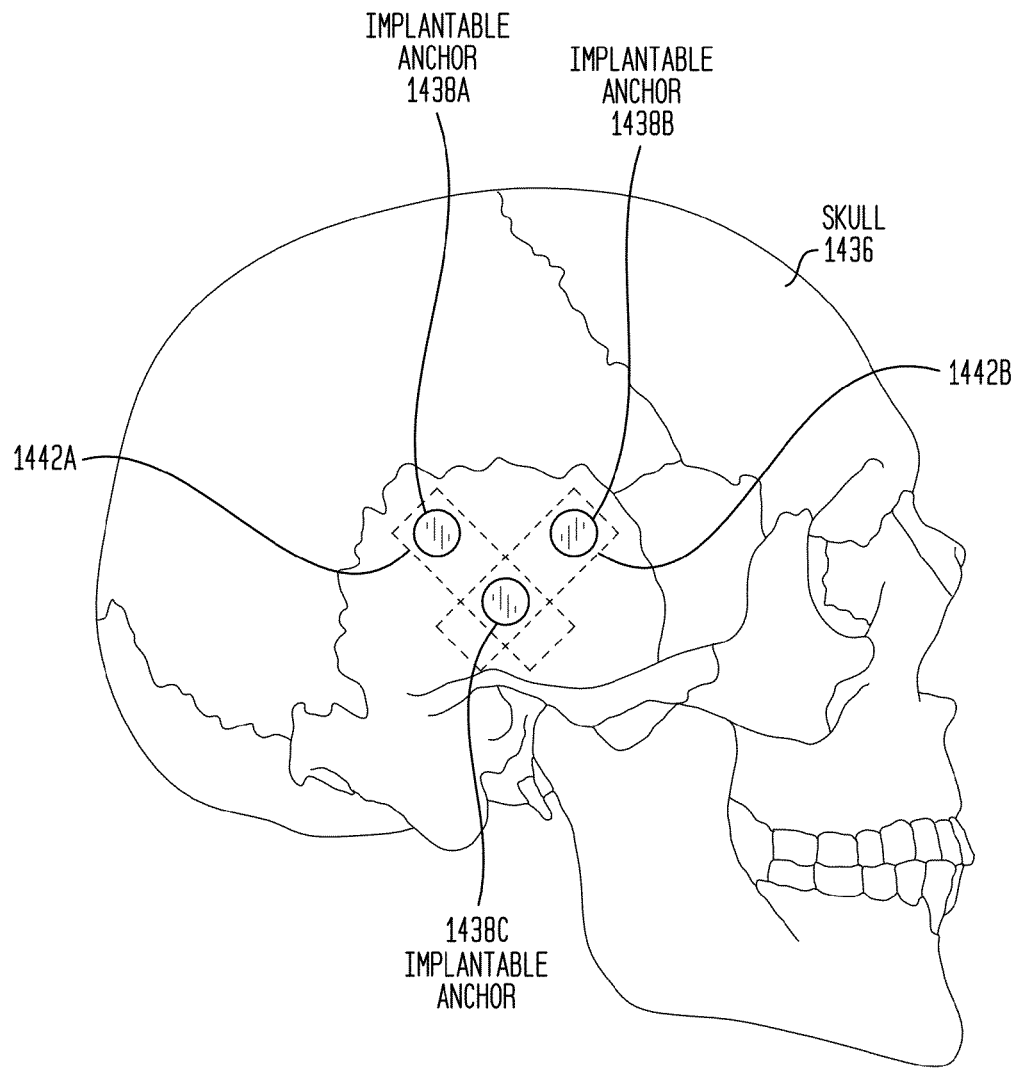

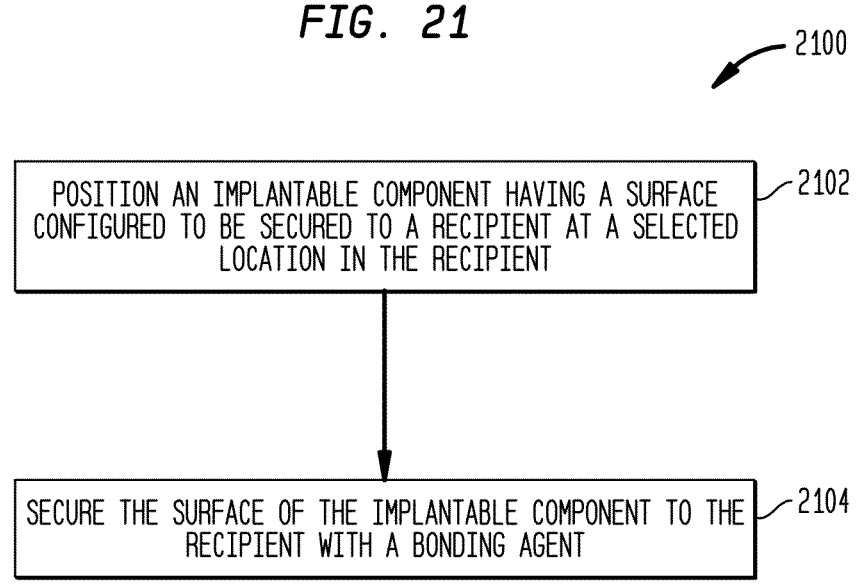

SECURABLE IMPLANTABLE COMPONENT

BACKGROUND

1. Field of the Invention

The present invention relates generally to an implantable component of a medical device, and more particularly, to a securable implantable component.

2. Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, direct acoustic stimulators, cochlear implants, auditory brain stimulators, etc.), functional electrical stimulation devices (e.g., implantable pacemakers, defibrillators, etc.), and other implantable medical devices, have been successful in performing life saving and/or lifestyle enhancement functions for a number of years. The types of implantable medical devices and the ranges of functions performed thereby have continued to increase over the years.

SUMMARY

In one aspect of the invention, an apparatus is provided. The apparatus comprises an implantable component configured to be implanted adjacent to tissue/bone and having a surface configured to be secured to the tissue/bone with a bonding agent.

In another aspect of the present invention, a method is provided. The method comprises positioning an implantable component having a surface configured to be secured to tissue/bone at a selected location on the tissue/bone, and securing the surface of the implantable component to the tissue/bone with a bonding agent.

BRIEF DESCRIPTION OF THE DRAWINGS

Embodiments of the present invention are described herein in conjunction with the accompanying drawings, in which:

FIG. 1 is a schematic diagram of one embodiment of an exemplary prosthetic hearing device, a transcutaneous bone conduction device, having an implantable component securable to a recipient with a bonding agent in accordance with embodiments of the present invention;

FIG. 2 is a schematic diagram illustrating further details of the transcutaneous bone conduction device of FIG. 1;

FIG. 6A is a cross-sectional view of an implantable anchor having a surface configured to be secured to a recipient with a bonding agent, in accordance with embodiments of the present invention;

FIG. 6B is a perspective view of the implantable anchor of FIG. 6A;

FIG. 9 is a schematic diagram of a transcutaneous bone conductive device having implantable anchors configured to be secured to a recipient with a bonding agent, in accordance with embodiments of the present invention;

FIGS. 14A-14D are side-views of a recipient's skull illustrating the implantation location of implantable anchors configured to be secured to a recipient with a bonding agent, in accordance with embodiments of the present invention;

FIG. 21 is a flowchart illustrating a method in accordance with embodiments of the present invention.

DETAILED DESCRIPTION

Figure 3A:
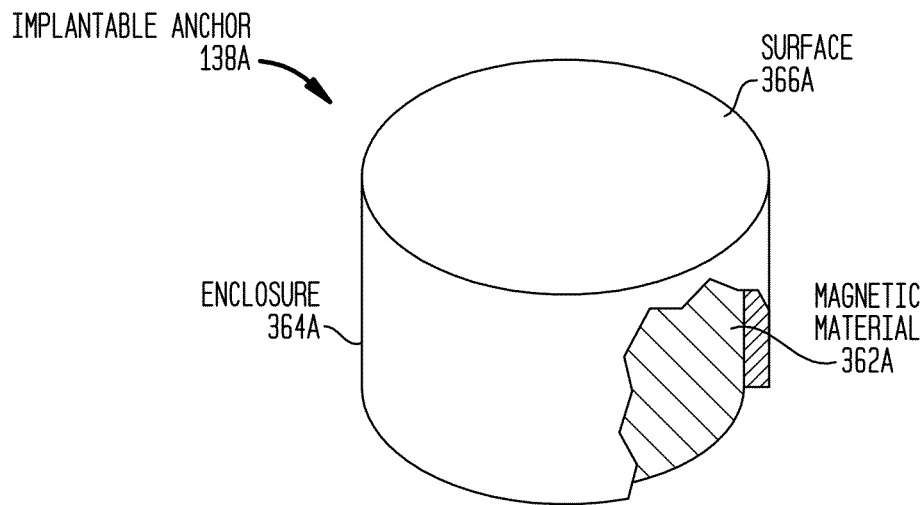
FIGS. 3A and 3B are partial cutaway, perspective views of implantable anchors having surfaces configured to be secured to a recipient with a bonding agent, in accordance with embodiments of the present invention.

Embodiments of the present invention are generally directed to implantable components configured to be secured to a recipient with a bonding agent. The implantable component is configured to be implanted adjacent to a recipient's bone and/or tissue and has a surface for attachment to the bonding agent.

Embodiments of the present invention are described herein primarily in connection with one type of implantable medical devices, namely hearing prostheses. Hearing prostheses include, but are not limited to, auditory brain stimulators, cochlear implants (also commonly referred to as cochlear implant devices, cochlear prostheses, and the like; simply "cochlear implants" herein), bone conduction devices, and direct acoustic stimulators. It is to be appreciated that embodiments of the present invention may be implemented in any implantable medical device now known or later developed.

FIG. 1 is a perspective view of a transcutaneous bone conduction device 100 in which embodiments of the present invention may be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 110 to vibrate. Such vibration sets up waves of fluid motion within cochlea 115 that, in turn, activates hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient.

Bone conduction device 100 comprises an external component 140 and implantable component 150. The external component 140 includes a sound input element 126 to receive sound signals. Sound input element 126 may comprise, for example, a microphone, telecoil, etc. Sound input element 126 may be located on or in bone conduction device 100, on a cable or tube extending from bone conduction device 100, etc. Alternatively, sound input element 126 may be subcutaneously implanted in the recipient, or positioned in the recipient's ear. Sound input element 126 may also be a component that receives an electronic signal indicative of sound, such as, for example, from an external audio device. For example, sound input element 126 may receive a sound signal in the form of an electrical signal from an MP3 player electronically connected to sound input element 126.

Bone conduction device 100 is an implantable medical device because, as noted above, it includes at least one implantable component 150 configured to be implanted in the recipient. As shown in FIG. 1 and described further below, the implantable component 150 comprises first and second implantable anchors 138A and 138B configured to be implanted adjacent to and abutting skull bone 136. Also as described further below, the first and second implantable anchors 138A and 138B are configured to be secured to the bone 136 via a bonding agent 142. Although FIG. 1 illustrates an embodiment that includes first and second implantable anchors 138A and 138B, it is to be appreciated that other embodiments may include a single anchor or more than two anchors.

FIG. 2 is a partial cross-sectional view illustrating further details of bone conduction 100 of FIG. 1. In these embodiments, sound input element 126 is mounted on a housing 252 of external component 140. Positioned in housing 252 are one or more operational components that include a sound processor 254 and a vibrating actuator 256. In operation, sound input device 126 converts received sounds into electrical signals. These electrical signals are utilized by the sound processor 254 to generate control signals that cause the actuator 256 to generate vibration. In other words, the actuator 256 converts the electrical signals into mechanical vibration. Also positioned in or attached to housing 252 is a plate 258 that is mechanically coupled to actuator 256. Plate 258 may be a permanent magnet or include magnetic material that generates and/or is reactive to a magnetic field.

As noted, the implantable component 150 comprises first and second implantable anchors 138A and 138B. Implantable anchors 138A and 138B each include magnetic material (i.e., a permanent magnet and/or other another element that generates and/or is reactive to a magnetic field) that forms a magnetic coupling with plate 258.

Because actuator 256 is mechanically coupled to plate 258, the vibrations are transferred from the actuator 256 to plate 258. Furthermore, because implantable anchors 138A and 138B are magnetically coupled to plate 258, vibration produced by the actuator 256 and transferred to plate 258 is transferred (via the magnetic coupling) across the recipient's tissue 131 that, as shown in FIGS. 1 and 2, may include one or more of the recipient's skin 132, fat 128, and muscle 134, to implantable anchors 138A and 138B. This transfer may occur via mechanical conduction of the vibration through the tissue 131 (resulting from the external component 140 being in direct contact with the tissue 131) and/or via the magnetic field between the plate 258 and the implantable anchors 138A and 138B.

In the embodiments of FIGS. 1 and 2, the implantable anchors 138A and 138B have a surface (not shown in FIGS. 1 and 2) that is configured to be secured to the bone 136 with bonding agent 142. In certain embodiments, the bonding agent 142 is a bone cement. The bone cement may be, for example, an ionomeric bone cement or a poly methyl methacrylate (PMMA) bone cement. In other embodiments, the bonding agent may be any biocompatible adhesive now known or later developed. In certain embodiments, the bonding agent may be configured to be resorbed by the recipient's tissue/bone after fibrotic encapsulation by the recipient's tissue/bone.

Figure 3B:
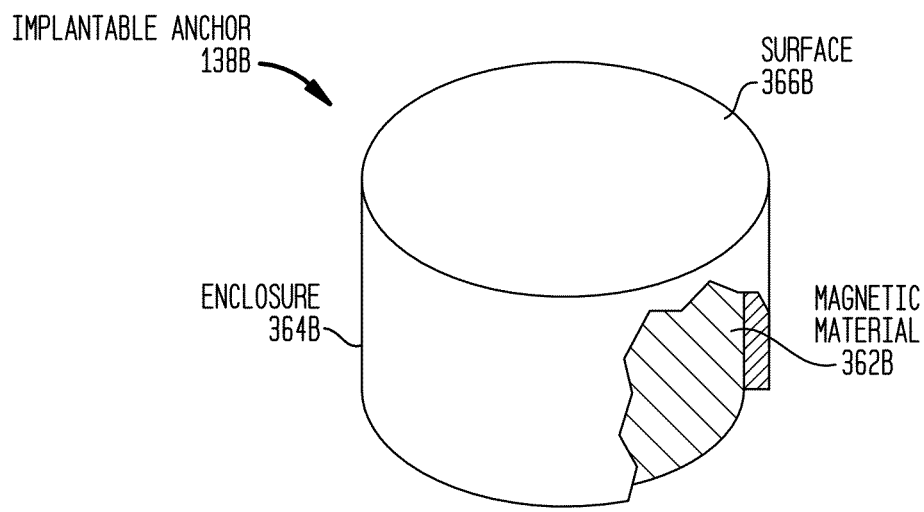

FIGS. 3A and 3B are partial cutaway, perspective views of implantable anchors 138A and 138B, respectively, in which a portion of an outer surface of the implantable anchors have been omitted for ease of illustration. In these embodiments, implantable anchors 138A and 138B comprise magnetic material (e.g., a magnet) 362A and 362B, respectively, disposed in an enclosure 364A and 364B, respectively. The enclosures 364A and 364B may comprise, for example, housings and/or silicone elastomer coatings. In certain embodiments, the enclosures 364A and 364B may each comprise a hermetic housing, such as a titanium housing.

FIGS. 3A and 3B illustrate surfaces 366A and 366B of enclosures 364A and 364B, respectively, which are each configured to be secured to bone 136 with a bonding agent 142. As described further below, the surfaces 366A and 366B may each have a shape configured to facilitate attachment of the bonding agent 142 to the surfaces or the surface 366A and 366B may each include surface features configured to facilitate attachment of the bonding agent 142 to the surfaces.

The surfaces 366A and 366B of implantable anchors 138A and 138B, respectively, are configured such that the attachment forces provided by bonding agent 142 to secure implantable anchors to bone 126 are sufficient such that the anchors can support the external component 140 via the magnetic coupling with plate 258. Additionally, the surfaces 366A and 366B of implantable anchors 138A and 138B, respectively, are configured such that the attachment forces provided by bonding agent 142 to secure implantable anchors to bone 126 are sufficient to transfer the vibration received from actuator 256 to the cochlea 115 via bone 136.

As noted above, a surface of an implantable component in accordance with embodiments of the present invention may have a shape configured to facilitate attachment of the bonding agent to the surface, or the surface may include surface features configured to facilitate attachment of the bonding agent to the surface. FIGS. 4A-8B illustrate exemplary surfaces having surface features to facilitate attachment of a bonding agent to the surface. For ease of illustration, FIGS. 4A-8B illustrate surface features in/on the surfaces of implantable anchors. It is to be appreciated that these and other surface features may be used in/on the surfaces of other implantable components to facilitate attachment of a bonding agent thereto.

Figure 4A:
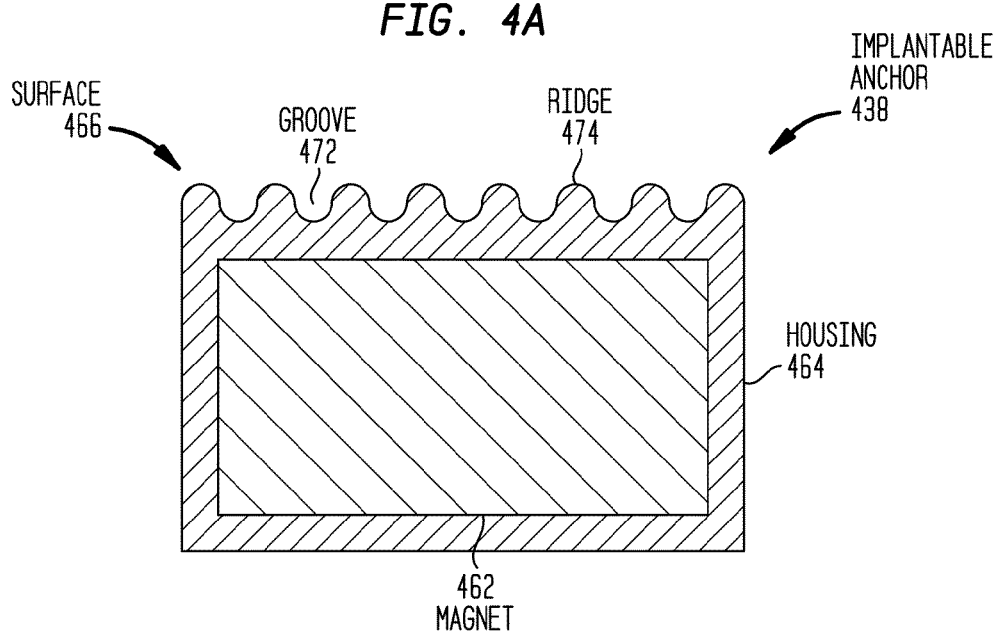
FIG. 4A is a cross-sectional view of an implantable anchor having a surface configured to be secured to a recipient with a bonding agent, in accordance with embodiments of the present invention.
Figure 4B:
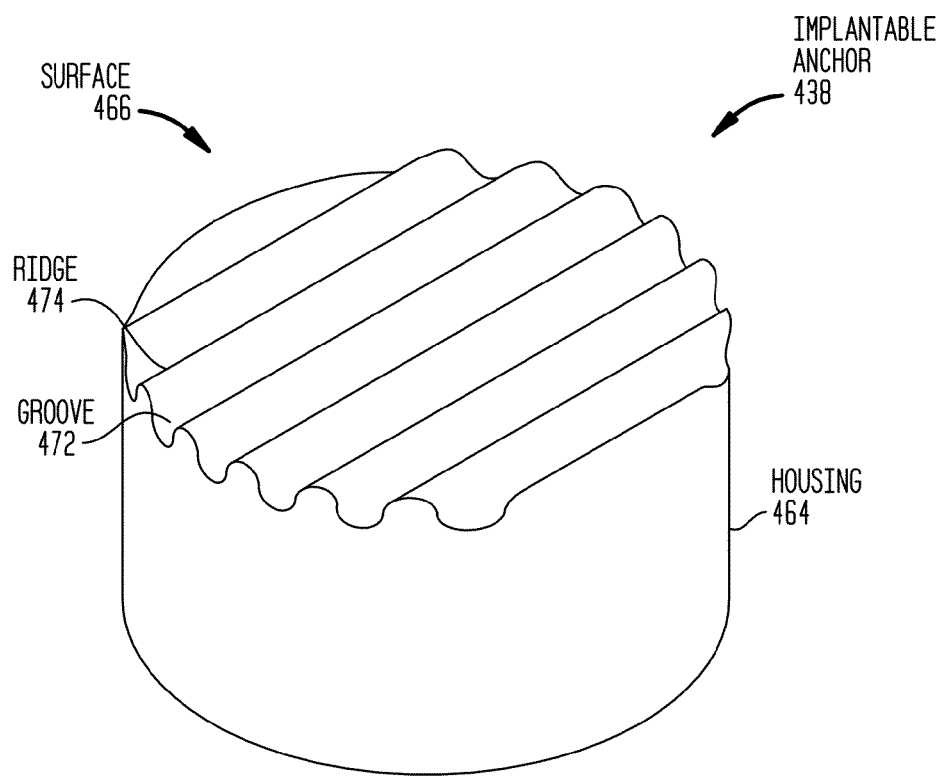
FIG. 4B is a perspective view of the implantable anchor of FIG. 4A.

FIG. 4A is a cross-sectional view of an implantable anchor 438 that comprises a magnet 462 positioned in a housing 464. FIG. 4B is a perspective view of the implantable anchor 464.

In the embodiments of FIGS. 4A and 4B, the implantable anchor 438 comprises a surface 466 configured to be secured to a recipient's bone with a bonding agent. Surface 466 is contoured to include a plurality of recesses in the form of spaced grooves or troughs 472 separated by ridges 474. The grooves 472 are, in this embodiment, elongate concave grooves having a radius of curvature and extending substantially across the surface 466. Similarly, the ridges 474 are, in this embodiment, elongate convex ridges having a radius of curvature and extend substantially across the surface 466. In general, the grooves 472 and ridges 474 function to increase the surface area of the surface 466 (relative to a planar surface) so as to increase the adhesion forces between a bonding agent and the surface 466. More specifically, the grooves are configured so that bonding agents used to secure surface 466 to a recipient's bone will substantially fill the grooves 472, thereby increasing the contact area between the bonding agent and the surface 466.

As noted, FIGS. 4A and 4B illustrate embodiments where the grooves 472 and ridges 474 extend substantially across the surface 466. It is to be appreciated that in alternative embodiments the grooves 472 and ridges 474 may only extend across one or more portions of the surface 466 to form a symmetrical or an asymmetrical arrangement of grooves/ridges.

FIGS. 4A and 4B illustrate a specific implementation where grooves 472 are used in combination with ridges 474. In certain embodiments, the grooves 472 may be formed through the creation of ridges 474 or vice versa. It is also to be appreciated that other embodiments of surface 466 may include only grooves 472 or only ridges 474.

Figure 5A:
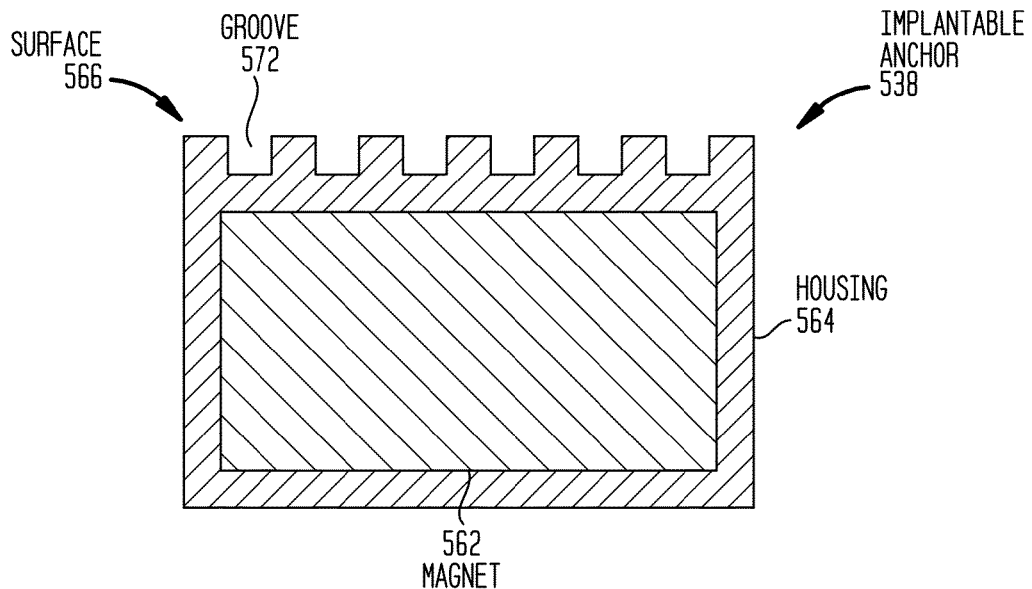
FIG. 5A is a cross-sectional view of an implantable anchor having a surface configured to be secured to a recipient with a bonding agent, in accordance with embodiments of the present invention.
Figure 5B:
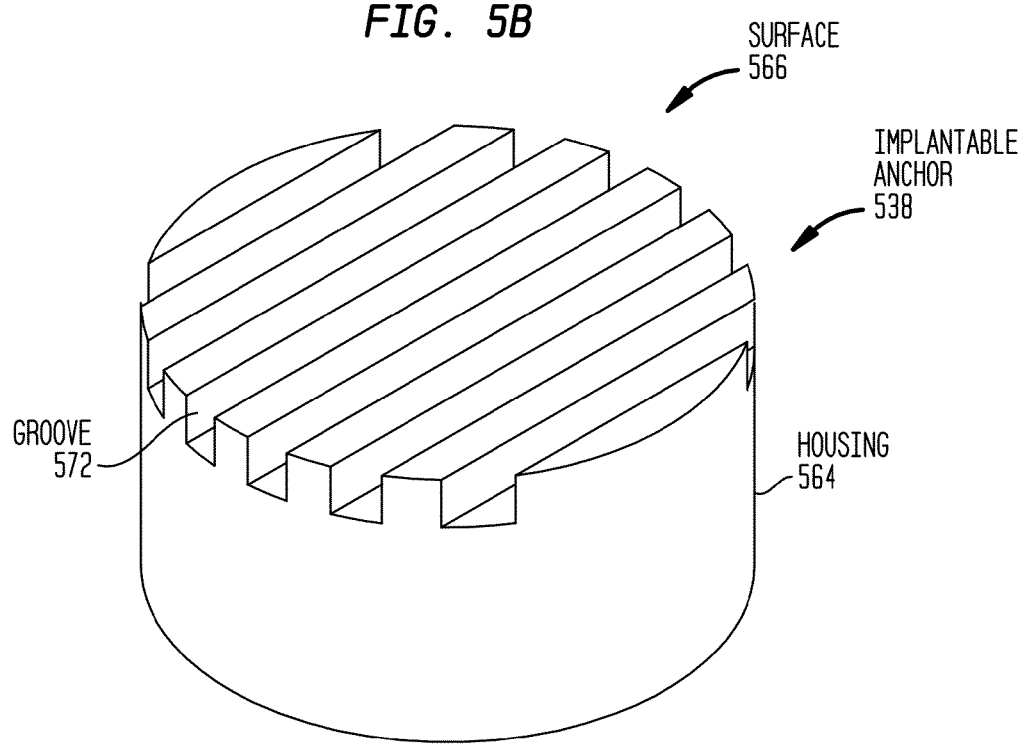
FIG. 5B is a perspective view of the implantable anchor of FIG. 5A.

FIGS. 5A and 5B illustrate an alternative embodiment of an implantable anchor in which a surface of includes grooves having a square cross-sectional shape, rather than a radius of curvature as shown in FIGS. 4A and 4B. FIG. 5A is a cross-sectional view of such an implantable anchor 538 that comprises a magnet 562 positioned in a housing 564. FIG. 5B is a perspective view of the implantable anchor 538.

In the embodiments of FIGS. 5A and 5B, the implantable anchor 538 comprises a surface 566 configured to be secured to a recipient's bone with a bonding agent. Surface 566 is contoured to include a plurality of recesses in the form of spaced grooves or channels 572. The grooves 572 are, in this embodiment, elongate grooves having a substantially square cross-sectional shape. The grooves 572 each extend substantially across the surface 566. In general, the grooves 572 function to increase the surface area of the surface 566 (relative to a planar surface) so as to increase the adhesion forces between a bonding agent and the surface 566. More specifically, the grooves 572 are configured so that bonding agents used to secure surface 566 to a recipient's bone will substantially fill the grooves 572, thereby increasing the contact area between the bonding agent and the surface 566.

As noted, FIGS. 5A and 5B illustrate embodiments where the grooves 572 extend substantially across the surface 566. It is to be appreciated that in alternative embodiments the grooves 572 may only extend across one or more portions of the surface 566 to form a symmetrical or asymmetrical arrangement of grooves.

Also as noted above, the grooves 572 of FIGS. 5A and 5B have a generally square cross-sectional shape. It is to be appreciated that the grooves 572 may also contain undercut regions. For example, FIGS. 6A and 6B are cross-sectional and perspective views, respectively, of an implantable anchor 638 having L-shaped grooves 672.

The L-shaped grooves 672 are disposed in a surface 666 configured to be secured to a recipient's bone with a bonding agent. The L-shaped grooves 672 comprise a first portion 680 and a second portion 682 that is substantially perpendicular to the first portion. The L-shaped grooves 672 also each extend substantially across the surface 666. In general, the undercut feature of grooves 672 function to create a mechanical lock, or an interlock between a bonding agent and the surface 666. More specifically, the L-shaped grooves 672 are configured so that bonding agents used to secure surface 666 to a recipient's bone will substantially fill the grooves 672, thereby increasing the contact area between the bonding agent and the surface 666.

The undercut portion of the L-shaped grooves 672 create a winding course that is followed by a bonding agent. That is, the bonding agent undergoes at least one turn when the bonding agent fills the L-shaped grooves 672. This at least one turn creates an interlock between the bonding agent and the surface 666 that increases the attachment forces provided by the bonding agent.

FIGS. 4A-6B illustrate several examples of grooves/ridges that may be formed in a surface of an implantable anchor. It is to be appreciated that alternative embodiments of the present invention may include grooves/ridges having different shapes and configurations. For example, grooves/ridges may have cross-sectional shapes that are rectangular, triangular, trapezoidal, etc. It is also to be appreciated that grooves in alternative embodiments may have geometries that include different undercut regions. For example, alternative grooves may be T-shaped, J-shaped, dovetailed, frustoconical, etc.

Figure 7A:
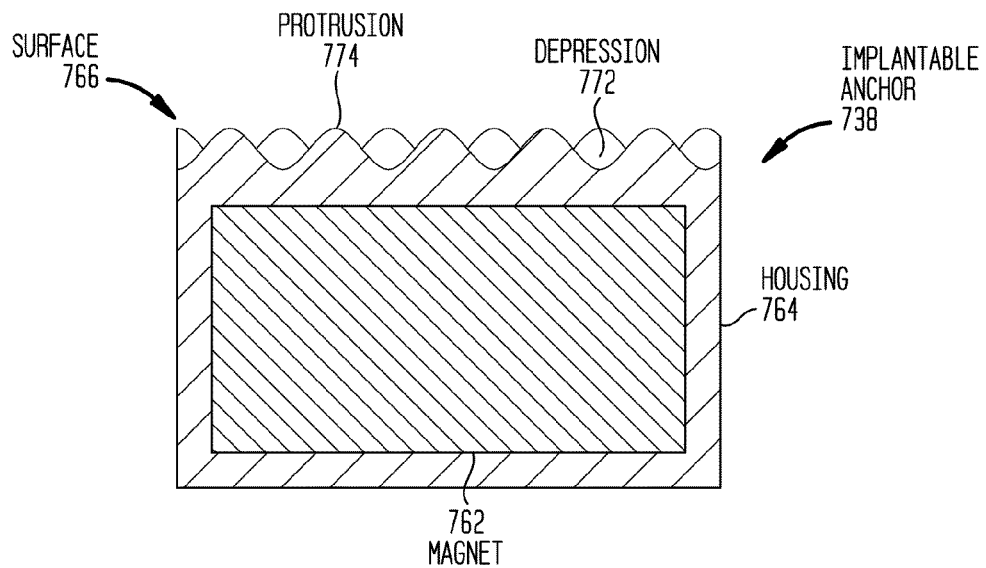
FIG. 7A is a cross-sectional view of an implantable anchor having a surface configured to be secured to a recipient with a bonding agent, in accordance with embodiments of the present invention.
Figure 7B:
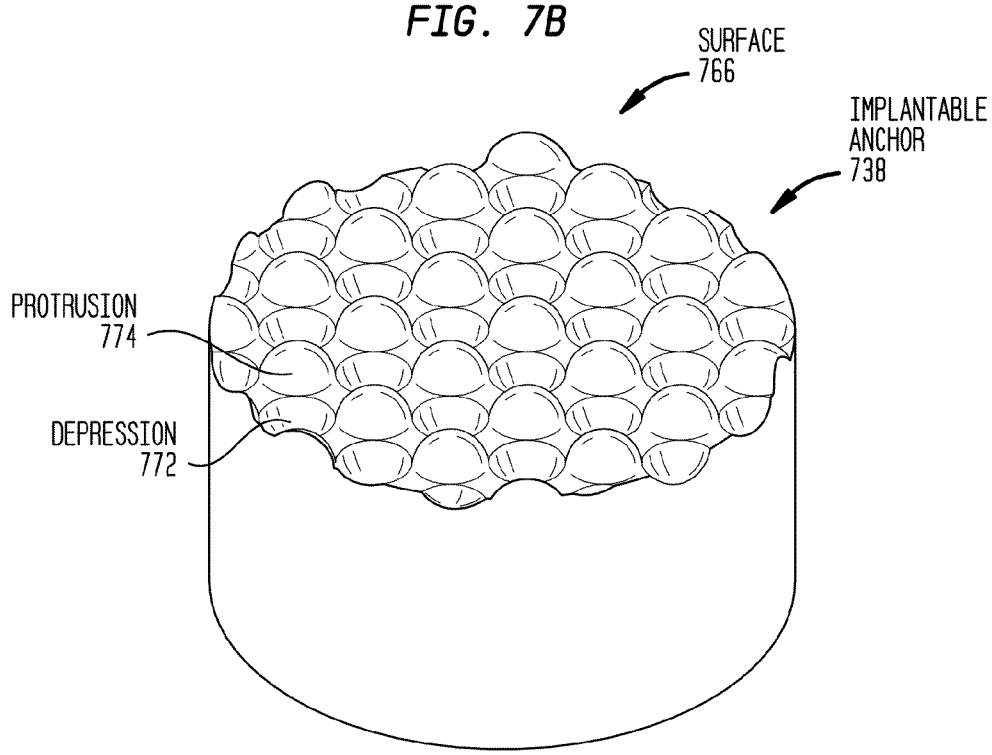
FIG. 7B is a perspective view of the implantable anchor of FIG. 7A.

FIG. 7A is a cross-sectional view of an implantable anchor 738 in accordance with further embodiments of the present invention that comprises a magnet 762 positioned in a housing 764. FIG. 7B is a perspective view of the implantable anchor 738.

In the embodiments of FIGS. 7A and 7B, the implantable anchor 738 comprises a surface 766 configured to be secured to a recipient's bone with a bonding agent. Surface 766 is contoured to include a plurality of recesses in the form of depressions 772 defined by spaced protrusions 774. The protrusions 774 have, as shown in FIGS. 7A and 7B, a generally parabolic or dome shape and are disposed across the surface 766. In general, the protrusions 774 function to increase the surface area of the surface 766 (relative to a planar surface) so as to increase the adhesion forces between a bonding agent and the surface 766. More specifically, depressions 772 and/or protrusions 774 are configured so that bonding agents used to secure surface 766 to a recipient's bone will substantially fill the depressions 772 defined by the protrusions 774, thereby increasing the contact area between the bonding agent and the surface 766.

As noted, FIGS. 7A and 7B illustrate embodiments with protrusions 774 having a generally parabolic shape. It is to be appreciated that alternative embodiments may use different shapes (i.e., square, rectangular, arcuate, etc.) for protrusions 774.

Also, FIGS. 7A and 7B illustrate a specific implementation where depressions 772 are used in combination with protrusions 774. In certain embodiments, the depressions 772 may be formed through the creation of protrusions 774 or vice versa. It is also to be appreciated that other embodiments of surface 766 may include only depressions 772 or only protrusions 774.

Figure 8A:
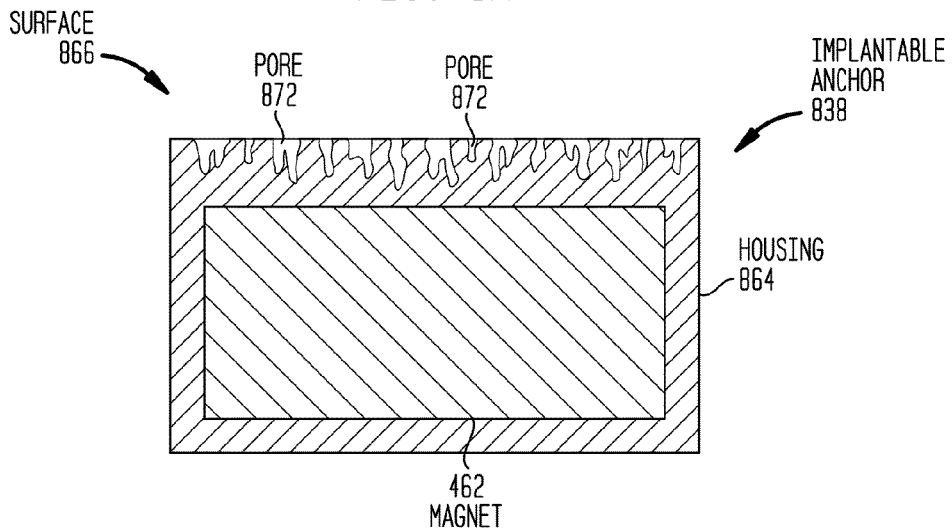
FIG. 8A is a cross-sectional view of an implantable anchor having a surface configured to be secured to a recipient with a bonding agent, in accordance with embodiments of the present invention.
Figure 8B:
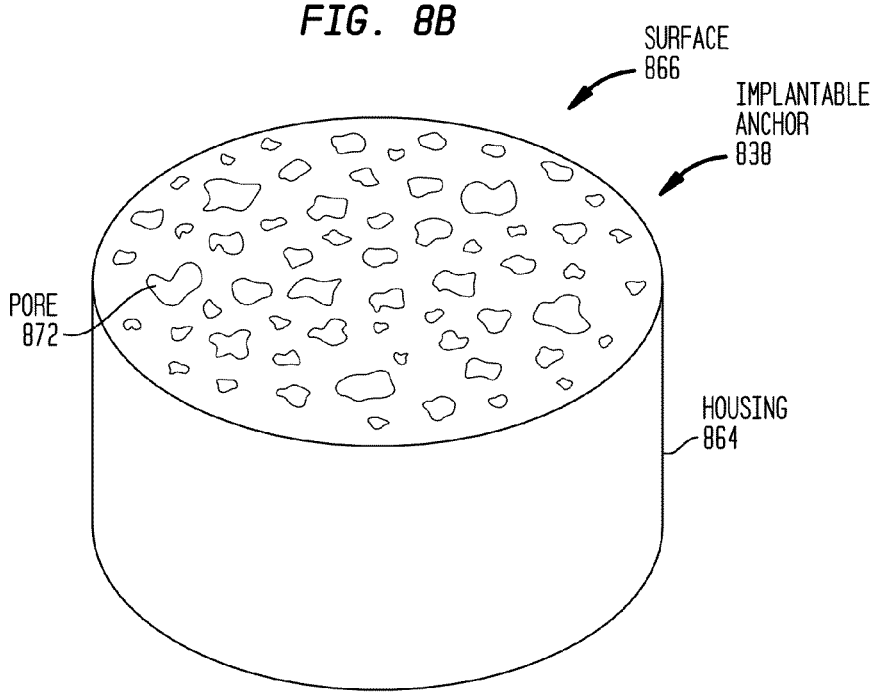
FIG. 8B is a perspective view of the implantable anchor of FIG. 8A.

FIG. 8A is a cross-sectional view of an implantable anchor 838 that comprises a magnet 862 positioned in a housing 864. FIG. 8B is a perspective view of the implantable anchor 838.

In the embodiments of FIGS. 8A and 8B, the implantable anchor 838 comprises a surface 866 configured to be secured to a recipient's bone with a bonding agent. Surface 866 is contoured to include a plurality of recesses in the form of pores 872. In general, the pores 872 function to increase the surface area of the surface 866 (relative to a planar surface) so as to increase the adhesion forces between a bonding agent and the surface 866. More specifically, the pores 872 are configured so that bonding agents used to secure surface 866 to a recipient's bone will substantially fill the pores 872, thereby increasing the contact area between the bonding agent and the surface 866.

Additionally, it is to be appreciated that the pores may have irregular shapes that potentially result in mechanical locking. That is, the irregular shape of the pores may cause the bonding agent to undergo one or more turns when the bonding agent fills the pores 872. As such, when a bonding agent fills the pores 872, the one or more turns create an interlock between the bonding agent and the surface 866 that increases the attachment forces provided by the bonding agent. In certain embodiments, the pores 872 may be chemically etched into the surface 866.

FIG. 9 is a schematic diagram illustrating a passive transcutaneous bone conduction device 900 in accordance with embodiments of the present invention implanted in a recipient. Similar to the embodiments of FIGS. 1 and 2, bone conduction device 900 comprises an external component 940 and an implantable component 950 comprising a first implantable anchor 938A and a second implantable anchor 938B configured to be implanted adjacent to the recipient's skull 136. Implantable anchors 938A and 938B are configured to be secured to the skull 936 with a bonding agent 942.

External component 940 comprises an actuator 956 that is mechanically coupled to an external plate 958 via a coupling 954. External component 940 may comprise additional elements such as a sound input element, housing, sound processor, etc., that, for ease of illustration, have been omitted from FIG. 9.

In operation, actuator 956 generates vibration that is transferred to plate 958. Plate 958 is magnetically coupled to implantable anchors 938A and 938B such that the vibration is transferred across the recipient's skin/tissue (i.e., fat, muscle, etc.) to the implantable anchors 938A and 938B. Because the implantable anchors 938A and 938B are secured to the skull 936, the vibration is further transferred to the recipient's cochlea via skull 936.

As shown in FIG. 9, a recipient's skull 936 may be curved at a location where it is desirable to position implantable anchors 938A and 938B. In certain circumstances, the radius of curvature of the skull 136 may be such that the vibration from plate 958 is transferred to only discrete portions 948A and 948B of implantable anchors 938A and 938B, respectively. Similarly, these discrete portions 948A and 948B may support a substantial portion of the weight of the external component 940 as a result of the magnetic coupling between plate 958 and implantable 948A and 948B. In other words, portions 948A and 948B may become undesirable pressure points that negatively affect one or more of the operation, the lifetime of the bone conduction device 900, and/or impact the comfort of the recipient. FIGS. 10A-10D are cross-sectional views embodiments of the present invention in which the implantable anchors have a shape configured to distribute the pressure resulting from the magnetic coupling and vibration received from an external component, such as external component 940.

Figure 10A:
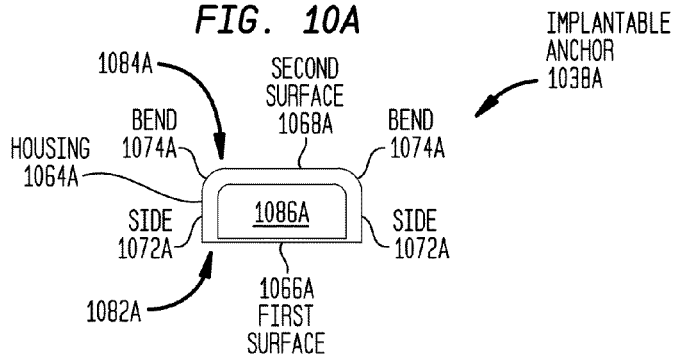
FIGS. 10A-10D are cross-sectional views of implantable anchors configured to be secured to a recipient with a bonding agent, in accordance with embodiments of the present invention.

FIG. 10A illustrates an implantable anchor 1038A comprising a housing 1064A. In this embodiment, housing 1064A has a rounded-cylindrical cross-sectional shape. More specifically, in this embodiment the housing 1064A has a first surface 1066A and a second surface 1068A that is positioned opposing the first surface 1066A. Second surface 1068A is connected to the first surface via arcuate bends 1074A and sides 1072A. When implanted, second surface 1068A is configured to be positioned adjacent to and facing the recipient's skin, while first surface 1066A is configured to be positioned adjacent to the recipient's skull and secured to the skull with a bonding agent.

In general, implantable anchor 1038A is referred to as comprising a first member 1082A that includes first surface 1066A and a second member 1084A that includes at least a portion of sides 1072A, second surface 1068A, and bends 1074A. The first and second members form a closed cavity 1086A in which a magnet (not shown) may be positioned. As a result of the shape of second member 1084A, forces applied as a result of operation with an external component (e.g., vibrational forces and magnetic forces) are distributed throughout the housing 1064A.

Figure 10B:
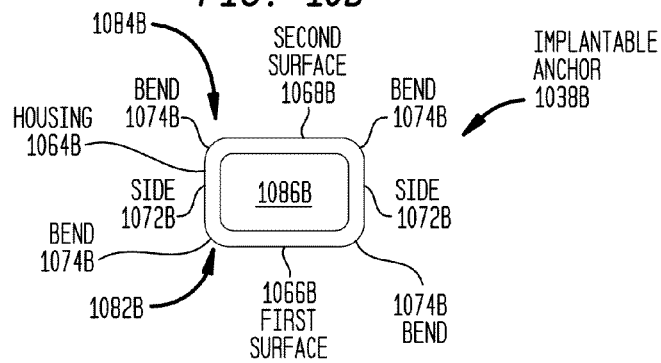

FIG. 10B illustrates an implantable anchor 1038B comprising a housing 1064B. In this embodiment, housing 1064B has a flattened-elliptical cross-sectional shape. More specifically, in this embodiment housing 1064B has a first surface 1066B and a second surface 1068B. Second surface 1068B is positioned opposing the first surface 1066B and is connected to the first surface via sides 1072B. Each of the first surface 1066B and the second surface 1068B is connected to the sides 1072B by arcuate bends 1074B. When implanted, second surface 1068B is configured to be positioned adjacent to and facing the recipient's skin, while first surface 1066B is configured to be positioned adjacent to the recipient's skull and secured to the skull with a bonding agent.

In general, implantable anchor 1038B is referred to as comprising a first member 1082B that includes first surface 1066B, at least a portion of sides 1072B, and the lower bends 1074B connecting first surface 1066B to sides 1072B. Implantable anchor 1038B is also referred to as comprising a second member 1084B that includes at least a portion of sides 1072B, second surface 1068B, and the upper bends 1074B connecting the second surface 1068B to the sides 1072B. The first and second members form a closed cavity 1086B in which a magnet (not shown) may be positioned. As a result of the shape of first and second members 1082B and 1084B, forces applied as a result of operation with an external component (e.g., vibrational forces and magnetic forces) are distributed throughout the housing 1064B.

Figure 10C:
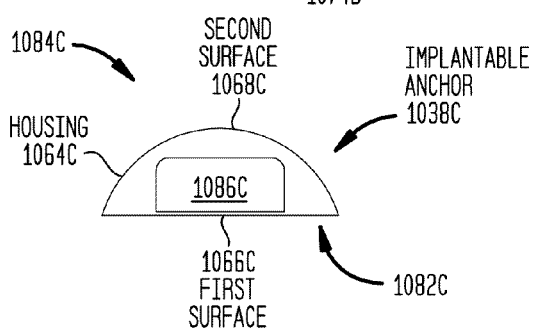

FIG. 10C illustrates an implantable anchor 1038C comprising a housing 1064C. In this embodiment, housing 1064C has a semi-circular cross-sectional shape. More specifically, housing 1064A has a generally planar first surface 1066C and a circular-arcuate second surface 1068C extended from the first surface 1066C. As such, implantable anchor 1038C has a general dome shape.

When implanted, second surface 1068C is configured to be positioned adjacent to and facing the recipient's skin, while first surface 1066C is configured to be positioned adjacent the recipient's skull and secured to the skull with a bonding agent. In general, implantable anchor 1038C is referred to as comprising a first member 1082C that includes first surface 1066C and a second member 1084C that includes second surface 1068C. The first and second members form a closed cavity 1086C in which a magnet (not shown) may be positioned. As a result of the shape of second member 1084C, forces applied as a result of operation with an external component (e.g., vibrational forces and magnetic forces) are distributed throughout the housing 1064C.

Figure 10D:
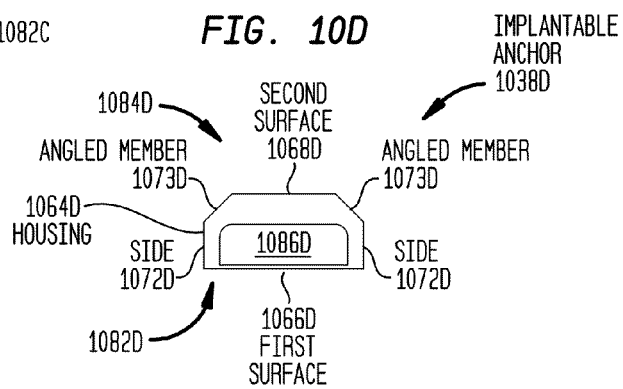

FIG. 10D illustrates an implantable anchor 1038D comprising a housing 1064D. In this embodiment, housing 1064D has a hexagonal cross-sectional shape. More specifically, the housing 1064D has a first surface 1066D and a second surface 1068D that is positioned opposing the first surface 1066D. The first surface 1066D is connected to sides 1072D, and the sides 1072D are connected to the second surface 1068D via angled members 1073D. When implanted, second surface 1068D is configured to be positioned adjacent to and facing the recipient's skin, while first surface 1066D is configured to be positioned adjacent to the recipient's skull and secured to the skull with a bonding agent.

In general, implantable anchor 1038D is referred to as comprising a first member 1082D that includes first surface 1066D and a second member 1084D that includes second surface 1068D, angled members 1073D, and at least a portion of sides 1072D. The first and second members form a closed cavity 1086D in which the magnet may be positioned. As a result of the shape of second member 1084D, forces applied as a result of operation with an external component (e.g., vibrational forces and magnetic forces) are distributed throughout the housing 1064D.

FIGS. 10A-10D illustrate several shapes of implantable anchors that may eliminate or substantially reduce discrete pressure points. It is to be appreciated that the shapes of FIGS. 10A-10D are merely examples and that other shapes may be used in alternative embodiments.

Figure 11:
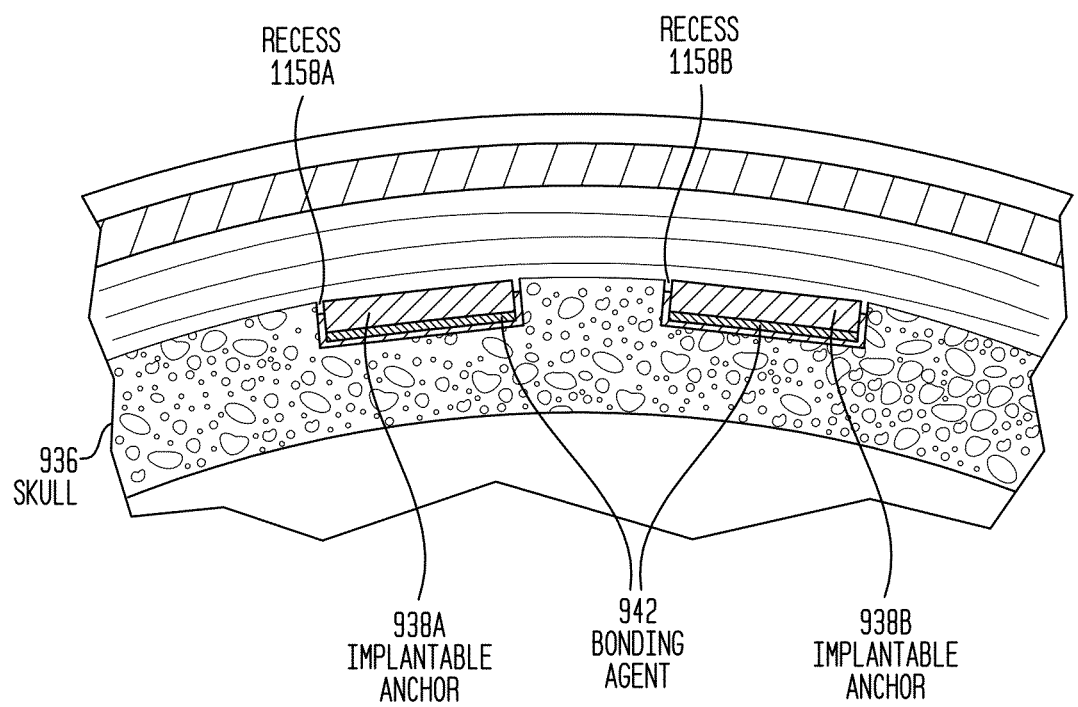
FIG. 11 is a schematic diagram illustrating the implantation of two implantable anchors configured to be secured to a recipient with a bonding agent, in accordance with embodiments of the present invention.

It is also to be appreciated that other techniques in accordance with embodiments of the present invention may be used to distribute the forces resulting from operation with an external component (e.g., vibrational forces and magnetic forces) to eliminate or substantially reduce discrete pressure points. FIG. 11 illustrates one such alternative technique where implantable anchors 938A and 938B of FIG. 9 are positioned in artificial recesses 1158A and 1158B, respectively, in skull 936. In these embodiments, the implantable anchors 938A and 938B are secured within the respective recess 1158A or 1158B with a bonding agent 942. If the implantable anchors 938A and 938B are fully recessed (i.e., do not extend past the openings of the recesses 1158A ad 1158B, respectively) the pressure from the external device will be primarily directed into the skull.

Figure 12A:
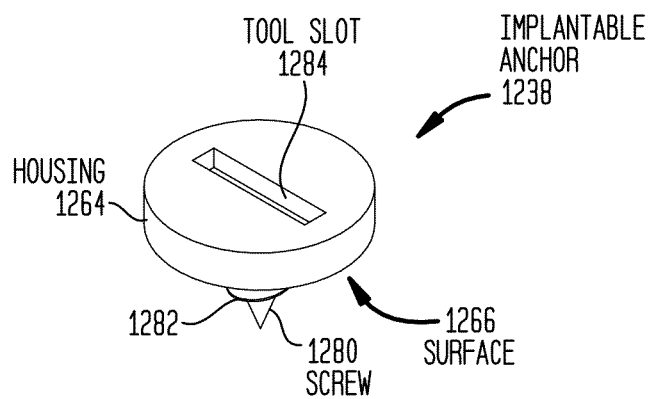
FIG. 12A is a perspective view of an implantable anchor having a surface configured to be secured to a recipient with a bonding agent, in accordance with embodiments of the present invention.
Figure 12B:
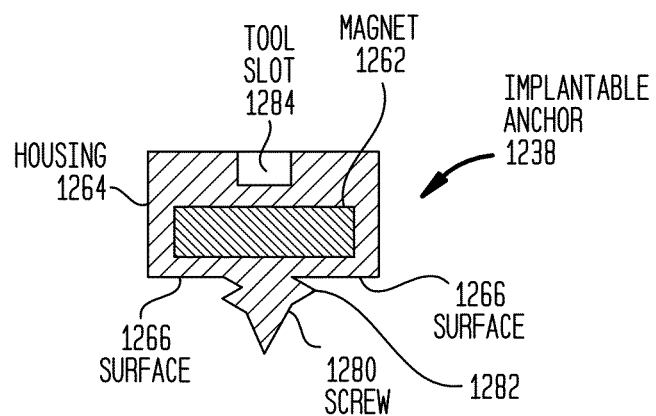
FIG. 12B is a cross-sectional view of the implantable anchor of FIG. 12A.

FIGS. 12A and 12B are perspective and cross-sectional views, respectively, of an implantable anchor 1238 configured to be secured to a recipient's bone with a bonding agent in accordance with embodiments of the present invention. Implantable anchor 1238 comprises a magnet 1262 positioned in a generally cylindrical housing 1264. The housing 1264 includes a surface 1266 configured to be secured to a recipient's bone with a bonding agent. Extending from the center of surface 1266 is a screw 1280 having threads 1282 configured to cut into, and mate with, the recipient's bone upon insertion of the screw 1280 into the bone.

Screw 1280 has a length that is sufficient to anchor the implantable anchor 1238 into the skull without penetrating entirely through the skull. The length of screw 1280 may depend, for example, on the thickness of the skull at the implantation site. In one embodiment, the screw 1280 has a length that is no greater than 5 mm, measured from the planar bottom surface 1266 to the distal end of screw 1280. In another embodiment, the length of the screw 1280 is the range of approximately 3.0 mm to approximately 5.0 mm.

As shown in FIGS. 12A and 12B, implantable anchor 1238 includes a tool slot 1284 that may be used for insertion of the screw 1280 into the bone. In operation, a surgeon or other medical practitioner inserts the screw 1280 into the bone using a tool that engages the tool slot 1284 such that the surface 1266 is adjacent to the bone. Prior to or during insertion of the screw 1280 into the bone, a bonding agent is applied to surface 1266 around the screw 1280. As such, when fully implanted, the surface 1266 is positioned adjacent to the bone and a bonding agent secures the surface 1266 to the bone around the screw 1280. In certain examples, because the screw 1280 is used in combination with a bonding agent, the screw 1280 may be significantly shorter than conventional bone screws such that the screw 1280 will not penetrate deeply into the recipient's bone. In one specific embodiment, the screw 1280 may include only one turn of a thread 1282 and be small relative to the magnet 1262.

Figure 13:
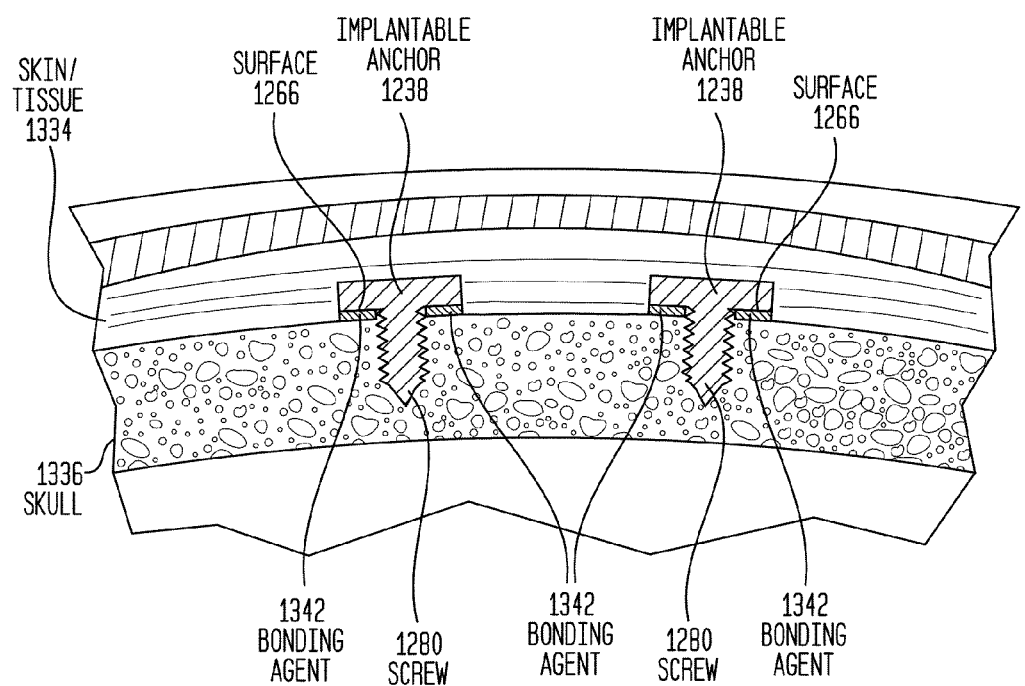
FIG. 13 is a schematic diagram illustrating the implantation of two of the implantable anchors of FIGS. 12A and 12B.

FIG. 13 is a cross-sectional view of a recipient's skull 1336 in which two implantable anchors 1238 in accordance with the embodiments of FIGS. 12A and 12B have been implanted. As shown, the screws 1280 are inserted into the skull 1336 so that surfaces 1266 are adjacent to the skull and beneath skin/tissue 1334. A bonding agent 1342 is positioned between the surfaces 1266 and the skull 1336 to secure the surfaces to the bone. In these embodiments, the use of the bonding agent 1342 may prevent loosening of screws 1280 after implantation.

Implantable anchors configured to be secured to a recipient's bone with a bonding agent may be implanted in a number of different locations and in various combinations. FIGS. 14A-14D are side-views of a recipient's skull 1436 and illustrate four arrangements of implanted implantable anchors. In the embodiments of FIGS. 14A-14D, the implantable anchors comprise magnetic material disposed in an enclosure (e.g., housing or coating).

Figure 14A:
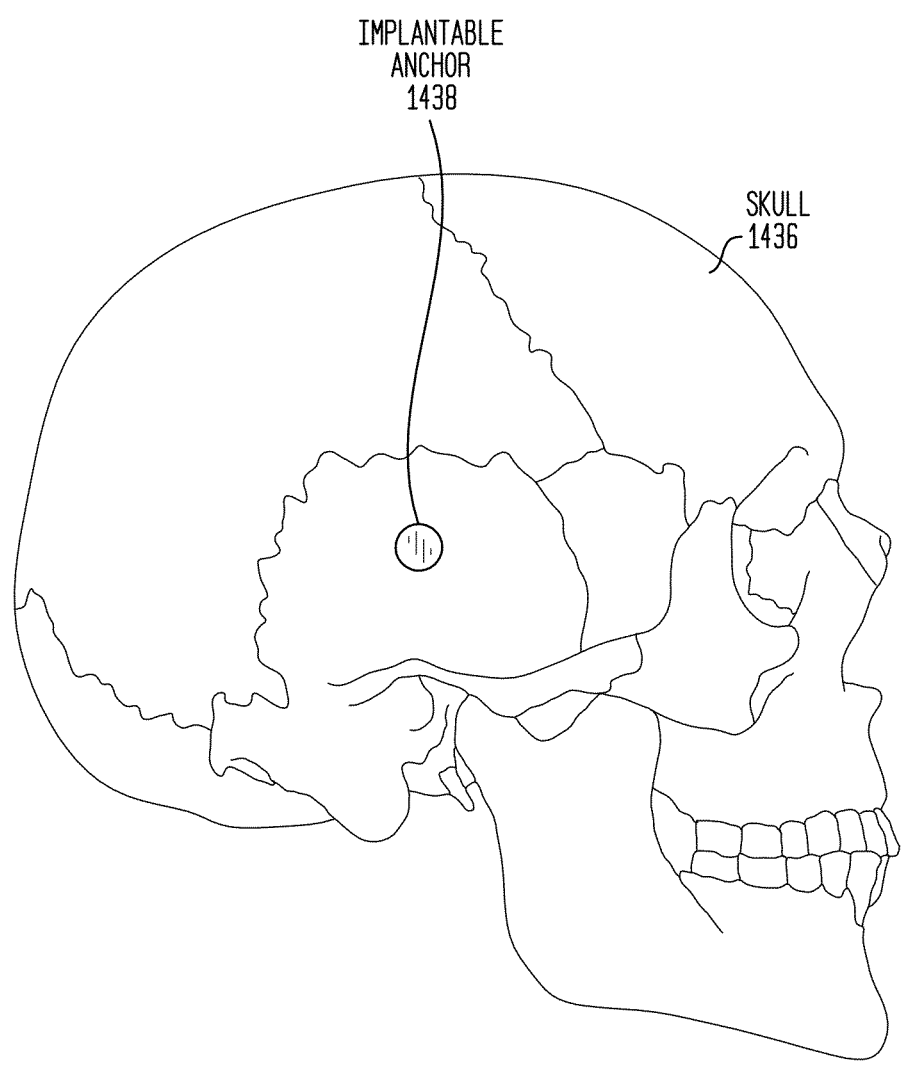

FIG. 14A illustrates an embodiment in which one implantable anchor 1438 is implanted into the recipient's skull 1436. In this embodiment, implantable anchor 1438 is configured to magnetically couple an external component to the recipient.

Figure 14B:
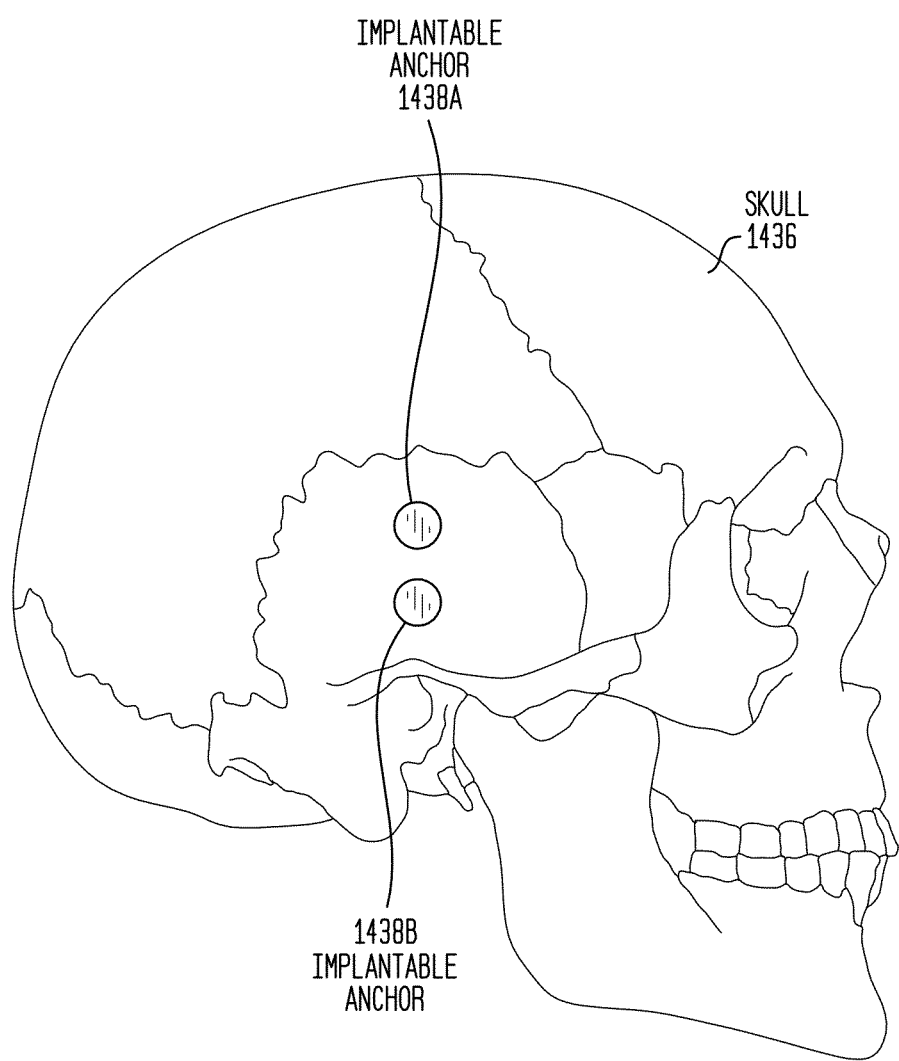

FIG. 14B illustrates another embodiment in which two implantable anchors 1438A and 1438B are implanted into the recipient's skull 1436 in a generally vertical arrangement (i.e., on top of one another). In alternative embodiments, implantable anchors 1438A and 1438B may be implanted in a generally horizontal arrangement (i.e., side-by-side), or at an alternate angle.

In one embodiment of FIG. 14B, implantable anchors 1438A and 1438B are configured to collectively couple an implantable component to the recipient. In other words, both implantable anchors are configured to be magnetically coupled to one or more magnetic plates positioned in an external component. In certain such embodiments, the magnetic materials in the implantable anchors 1438A and 1438B may have the same magnetic polarity. Alternatively, the magnetic materials in the implantable anchors 1438A and 1438B may have opposing magnetic polarity, or at least opposing magnetic-polarity on the portions facing the skin, so that the external component may only be positioned on the recipient in a pre-selected orientation. That is, one of the implantable anchors includes a magnet with a north pole facing the skin, while the second implantable anchor has a magnet with a south pole facing the skin.

In an alternative embodiment, only one of the implantable anchors 1438A and 1438B may be used at a time to magnetically couple an external component to the recipient. In such embodiments, the magnetic material in the implantable anchors 1438A and 1438B may have the same polarity facing the recipient's skin.

FIG. 14C illustrates an embodiment in which three implantable anchors 1438A, 1438B, and 1438C are implanted into the recipient's skull 1436. Implantable anchors 1438A and 1438B are generally positioned in a horizontal arrangement Implantable anchor 1438C is positioned below the implantable anchors 1438A and 1438B at point that is equidistant from the implantable anchors 1438A and 1438B. Alternatively, implantable anchor 1438C may be disposed above the implantable anchors 1438A and 1438B at point that is equidistant from the implantable anchors 1438A and 1438B. In still other embodiments, the three implantable anchors 1438A, 1438B, and 1438C are implanted all equidistant from another so as to form, for example, a triangular configuration.

In embodiments of FIG. 14C, two of the implantable anchors 1438A, 1438B, and 1438C may be used at any one time to magnetically couple an external component to the recipient. The magnetic materials in the implantable anchors 1438A, 1438B, and 1438C may each have a magnetic polarity, or at least a magnetic polarity on the portions facing the skin, so that the external component may only be positioned on the recipient in pre-selected orientations. More specifically, in one embodiment implantable anchors 1438A and 1438B may have the same polarity (e.g., outward facing north pole) while the implantable anchor 1438C may have the opposing polarity (e.g., outward facing south pole). As such, the combination 1442A (implantable anchors 1438A and 1438C) may be used to couple an external component to the recipient or the combination 1442B (implantable anchors 1438B and 1438C) may be used to couple an external component to the recipient.

Figure 14D:
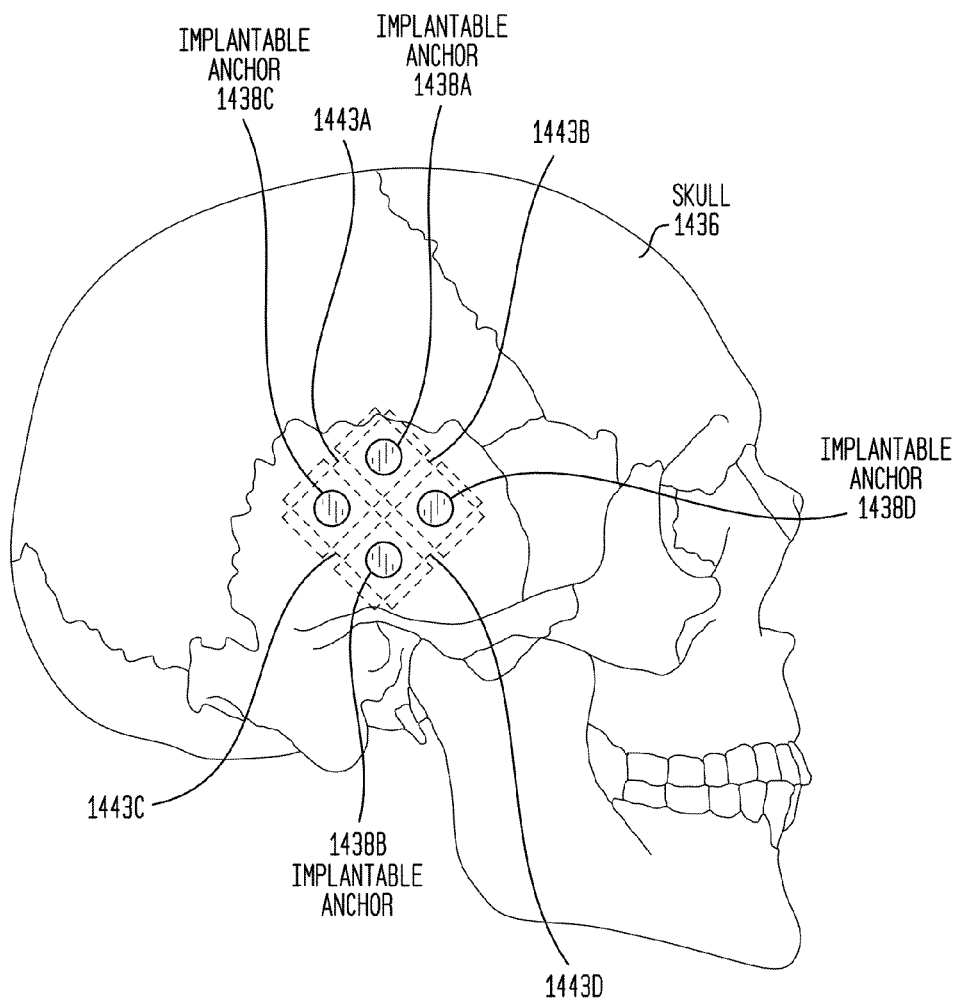

FIG. 14D illustrates an embodiment in which four implantable anchors 1438A, 1438B, and 1438C, and 1438D are implanted into the recipient's skull 1436. Implantable anchors 1438A and 1438B are generally positioned in a vertical arrangement, while implantable anchors 1438C and 1438D are generally positioned in a horizontal arrangement. More specifically, implantable anchor 1438B is positioned below the implantable anchors 1438C and 1438D at point that is equidistant from the implantable anchors 1438C and 1438D. Similarly, implantable anchor 1438A is positioned above the implantable anchors 1438C and 1438D at point that is equidistant from the implantable anchors 1438C and 1438D.

In embodiments of FIG. 14D, two of the implantable anchors 1438A, 1438B, 1438C, and 1438D are used at any one time to magnetically couple an external component to the recipient. The magnetic materials in the implantable anchors 1438A, 1438B, 1438C, and 1438D may each have a magnetic polarity, or at least a magnetic polarity on the portions facing the skin, so that the external component may only be positioned on the recipient so as to have pre-selected orientations. More specifically, implantable anchors 1438A and 1438B have the same polarity (e.g., outward facing north poles) while the implantable anchors 1438C and 1438D have the opposing polarity (e.g., outward facing south poles). As such, four different combinations of two of the implantable anchors 1438A, 1438B, 1438C, and 1438D may be used to couple an external component to the recipient. These combinations include combination 1443A (implantable anchors 1438A and 1438C), combination 1443B (implantable anchors 1438A and 1438D), combination 1443C (implantable anchors 1438C and 1438B), and combination 1443D (implantable anchors 1438B and 1438D).

It is to be appreciated that a recipient of a bone conduction device generally needs to use the device for extended periods of time on a daily basis to facilitate hearing enhancement. When the bone conduction device is in use, an external component is typically magnetically coupled to the recipient's head. However, such extended and daily use of an external component may cause skin/tissue necrosis, skin damage (i.e., cracking), or other issues. Such problems may be a result of the magnetic pressure applied as a result of the magnetic coupling and/or as a result of the transfer of vibration across the skin. As noted, the embodiments of FIGS. 14C and 14D provide different combinations of implantable anchors may be independently used to couple an external component to a recipient. As such, in these embodiments a recipient may adjust/change the location of the external component periodically (e.g., daily) so that different portions of the skin/tissue are subjected to the magnetic coupling/vibration. This may help prevent or substantially reduce skin/tissue damage resulting from the use of the external component.

In an alternative embodiment of FIG. 14C and FIG. 14D, all magnetic materials in the implantable anchors 1438A, 1438B, 1438C, and 1438D may have the same magnetic polarity, or at least a magnetic polarity on the portions facing the skin, so that the external component may be positioned on the recipient in a wider range of orientations. A range of one, two, three, or, with respect to FIG. 14C, all four magnets may be used to couple an external component to the recipient. In these and other embodiments a recipient may adjust/change the location of the external component for example to exclude one or more magnet from use for a period of time (e.g., a week). This may facilitate healing of any skin/tissue issues/damage resulting from the use of the external component while allowing the recipient to continue to derive benefits from use of the external component.

Figure 15:
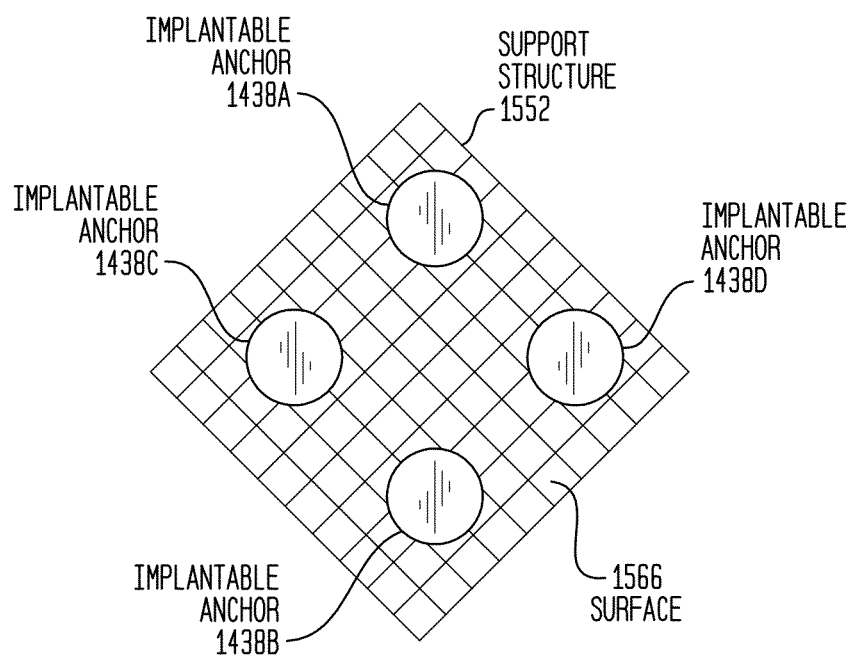
FIG. 15 is a top-view illustrating a plurality of anchors attached to a support structure configured to be secured to a recipient with a bonding agent, in accordance with embodiments of the present invention.

In certain embodiments that use multiple implantable anchors, such as the embodiments of FIG. 14D, a surgeon may have difficulty positioning the implantable anchors at the locations needed to provide the multiple combinations useable for independently coupling an external component to the recipient. As such, embodiments of the present invention may include implantable anchors pre-mounted on a support structure in a selected arrangement to facilitate accurate placement for implantation of the anchors into a recipient. In other words, in such embodiments the implantable anchors may be pre-positioned on a support structure with selected distances and polarities so as to provide various coupling arrangements for an external component. FIG. 15 is a top view of one embodiment in which implantable anchors 1438A-1438D of FIG. 14 are pre-mounted on a support structure 1552 for implantation into a recipient. In accordance with embodiments of the present, the support structure 1552 has a surface 1566 that is configured to be secured to the recipient's bone with a bonding agent. In certain embodiments, the surface 1566 may have any of the surface features described with reference to FIGS. 4A-8B or other surface features configured to facilitate attachment of the bonding agent to the support structure 1552.

Support structure 1552 may be formed from a variety of materials and may have a number of different arrangements. In one embodiment of the present invention, support structure 1552 is a mesh. The mesh may be substantially flexible or, in alternative embodiments, substantially rigid. The mesh may be further configured to osseointegrate with the recipient's bone over a period of time. In other embodiments, the mesh may be configured to be resorbed by the recipient's bone/tissue after fibrotic encapsulation (e.g., a bioresorbable mesh).

Figure 16A:
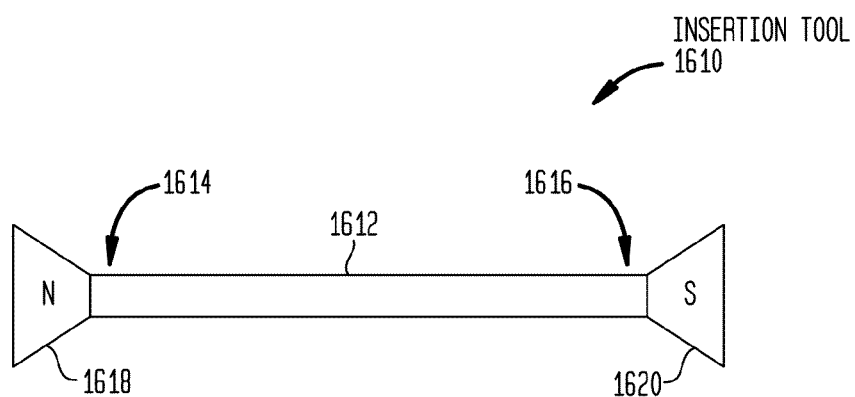
FIGS. 16A and 16B are side-views of an implantable anchor insertion tool, in accordance with embodiments of the present invention.

FIGS. 16A and 16A are side-views of an insertion tool 1610 that may be used to secure implantable anchors to a recipient's bone with a bonding agent in accordance with embodiments of the present invention. As shown, insertion tool 1610 comprises an elongate member 1612 having a proximal end 1614 and a distal end 1616. A magnetic member 1618 is disposed on the proximal end 1614 and a magnetic member 1620 is disposed on the distal end 1620.

Figure 16B:
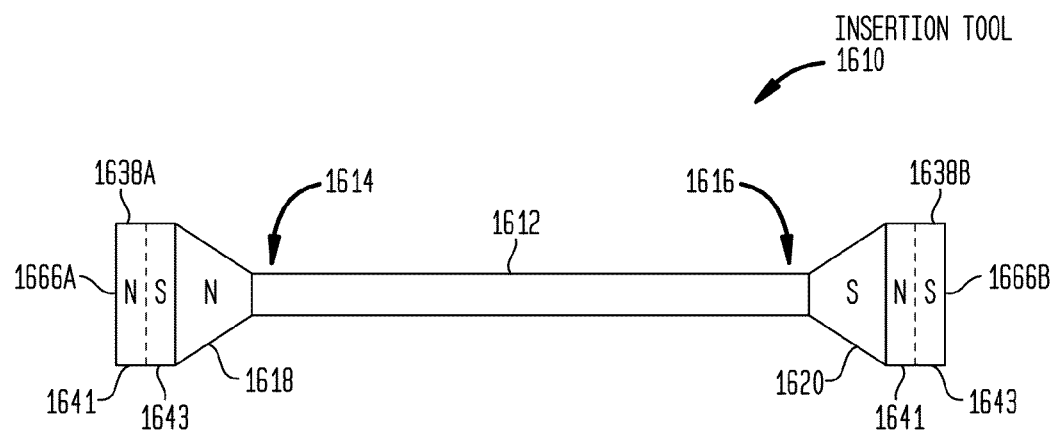

As shown in FIG. 16B, the magnetic members 1618 and 1620 are each configured to be magnetically coupled to an implantable anchor 1638A and 1638B, respectively, for implantation of the implantable anchors into a recipient Implantable anchors 1638A and 1638B each comprise a portion 1641 having a magnetic north polarity (i.e., a north pole of a magnet) and a portion 1643 having an opposing magnetic south polarity (i.e., a south pole of a magnet). As noted above, embodiments of the present invention that use multiple implantable anchors may need the implantable anchors to be implanted in a manner such that a certain magnetic polarity faces outwards or away from the recipient's bone. As such, magnetic member 1618 has a polarity (or at least a polarity in the portion facing away from proximal end 1614) that is opposite from the polarity of magnetic member 1620 (or at least opposite the polarity of the portion facing way from distal end 1616). In the example of FIGS. 16A and 16B, magnetic member 1618 has a magnetic north polarity and magnetic member 1620 has a magnetic south polarity.

As a result of the opposing polarities of magnetic members 1618 and 1620, the implantable anchors may be coupled to the insertion tool 1610 in a manner that prevents misplacement and subsequent incorrect polarity of the anchors when implanted. As shown in FIG. 16B, portion 1643 of implantable anchor 1638A is configured to be coupled to magnetic member 1618 so that a surface 1666A faces outward or away from the insertion tool 1610. Similarly, portion 1641 of implantable anchor 1638B is configured to be coupled to magnetic member 1618 so that a surface 1666B faces outward or away from the insertion tool 1610. As described further below, surfaces 1666A and 1666B are configured to be secured to a recipient's bone with a bonding agent.

Figure 17:
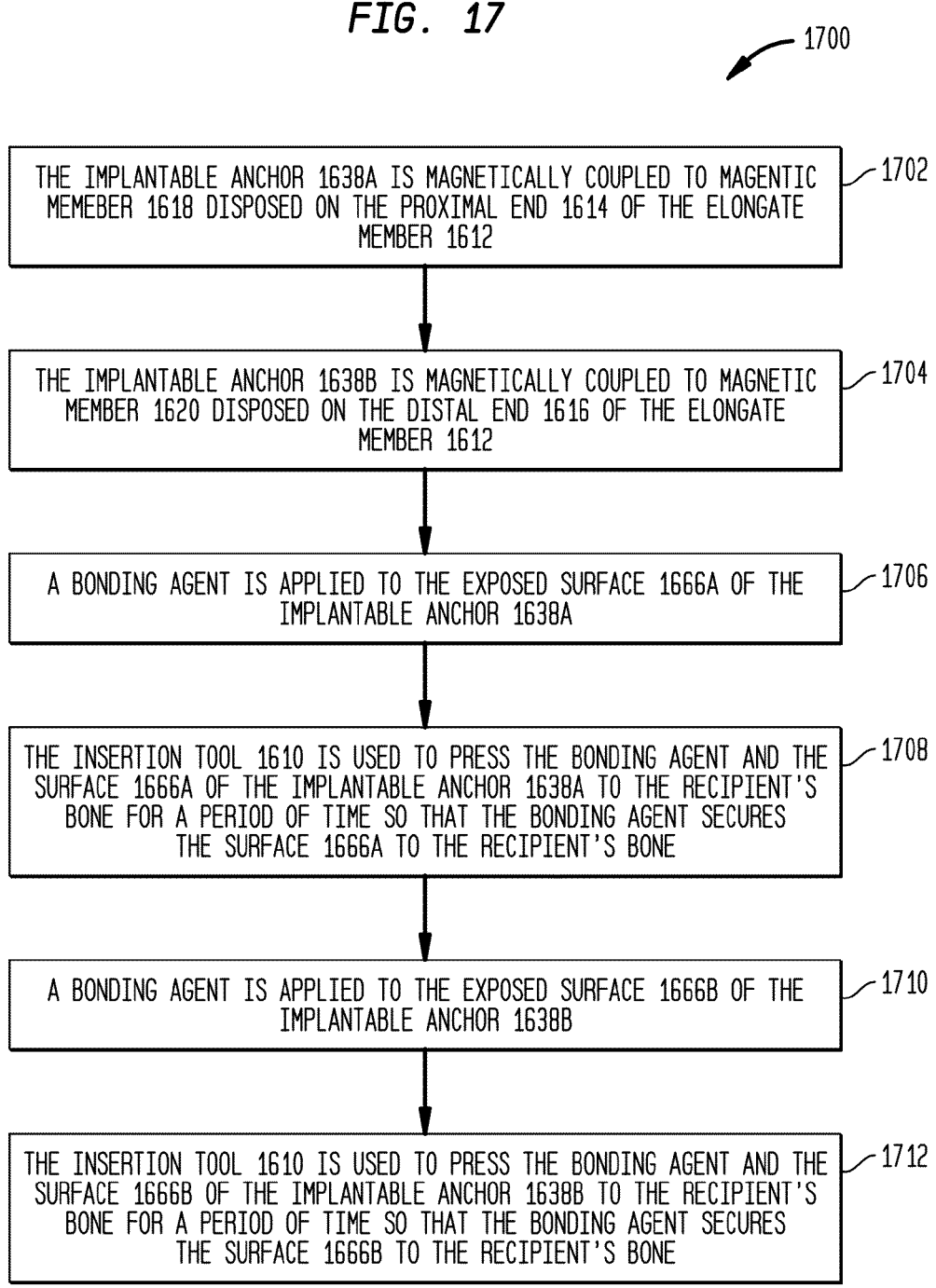
FIG. 17 is a flowchart illustrating a method for using the insertion tool of FIGS. 16A and 16B to secure two implantable anchors to a recipient's skull with a bonding agent, in accordance with embodiments of the present invention.

FIG. 17 is a flowchart illustrating a method 1700 for using insertion tool 1610 to secure implantable anchors 1638A and 1638B to a recipient's bone with a bonding agent. Method 1700 begins at step 1702 where the implantable anchor 1638A is magnetically coupled to magnetic member 1618 disposed on the proximal end 1614 of the elongate member 1612. As noted above, implantable anchor 1638A is magnetically coupled to magnetic member 1618 such that surface 1666A is exposed (i.e., faces outward from the insertion tool 1610). At step 1704, the implantable anchor 1638B is magnetically coupled to magnetic member 1620 disposed on the distal end of the elongate member 1612. As noted above, implantable anchor 1638B is magnetically coupled to magnetic member 1620 such that surface 1666B is exposed (i.e., faces outward from the insertion tool 1610).

At step 1706, a bonding agent is applied to the exposed surface 1666A of the implantable anchor 1638A. At step 1708, the insertion tool is used to press the bonding agent and the surface 1666A of the implantable anchor 1638A against the recipient's bone for a period of time so that the bonding agent secures the surface 1666A to the recipient's bone. The bonding agent is configured to create an attachment force between the surface 1666A of the implantable anchor 1638A and the bone that exceeds the force of the magnetic coupling between the implantable anchor 1638A and the magnetic member 1618. After a period of time (e.g., 10 minutes) that is sufficient for the bonding agent to secure the surface 1666A to the bone, the pressure is released and the insertion tool 1610 is removed leaving the implantable anchor 1638A secured to the recipient's bone.

At step 1710, a bonding agent is applied to the exposed surface 1666B of the implantable anchor 1638B. At step 1712, the insertion tool is used to press the bonding agent and the surface 1666B of the implantable anchor 1638B against the recipient's bone for a period of time so that the bonding agent secures the surface 1666B to the recipient's bone. The bonding agent is configured to create an attachment force between the surface 1666B of the implantable anchor 1638B and the bone that exceeds the force of the magnetic coupling between the implantable anchor 1638B and the magnetic member 1620. After a period of time (e.g., 10 minutes) that is sufficient for the bonding agent to secure the surface 1666B to the bone, the pressure is released and the insertion tool 1610 is removed leaving the implantable anchor 1638B secured to the recipient's bone.

Figure 18:
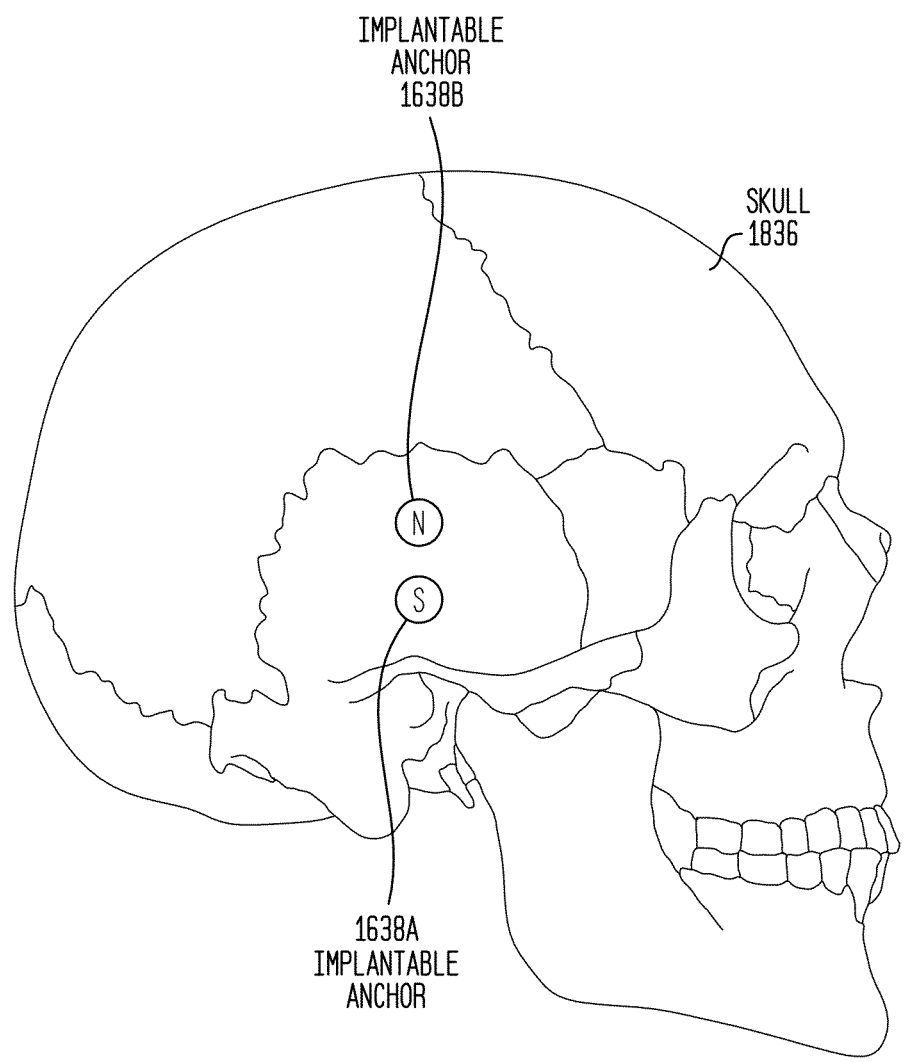
FIG. 18 is a side-view of a recipient's skull illustrating the magnetic configuration of two implantable anchors, in accordance with embodiments of the present invention.

FIG. 18 is a side-view of a recipient's skull 1836 illustrating the implantable anchors 1638A and 1638B after implantation according to the method of FIG. 17. As shown, the implantable anchors 1638A and 1638B having opposing outward facing polarities (e.g., one north and one south) for proper orientation of an external component magnetically coupled thereto.

Embodiments of the present invention have been primarily described with reference to the securement of implantable anchors for use with a bone conduction device to a recipient's skull with a bonding agent. As noted elsewhere herein, embodiments of the present invention are directed to the securement of any of a number of different implantable components to a recipient's bone with a bonding agent.

Figure 19:
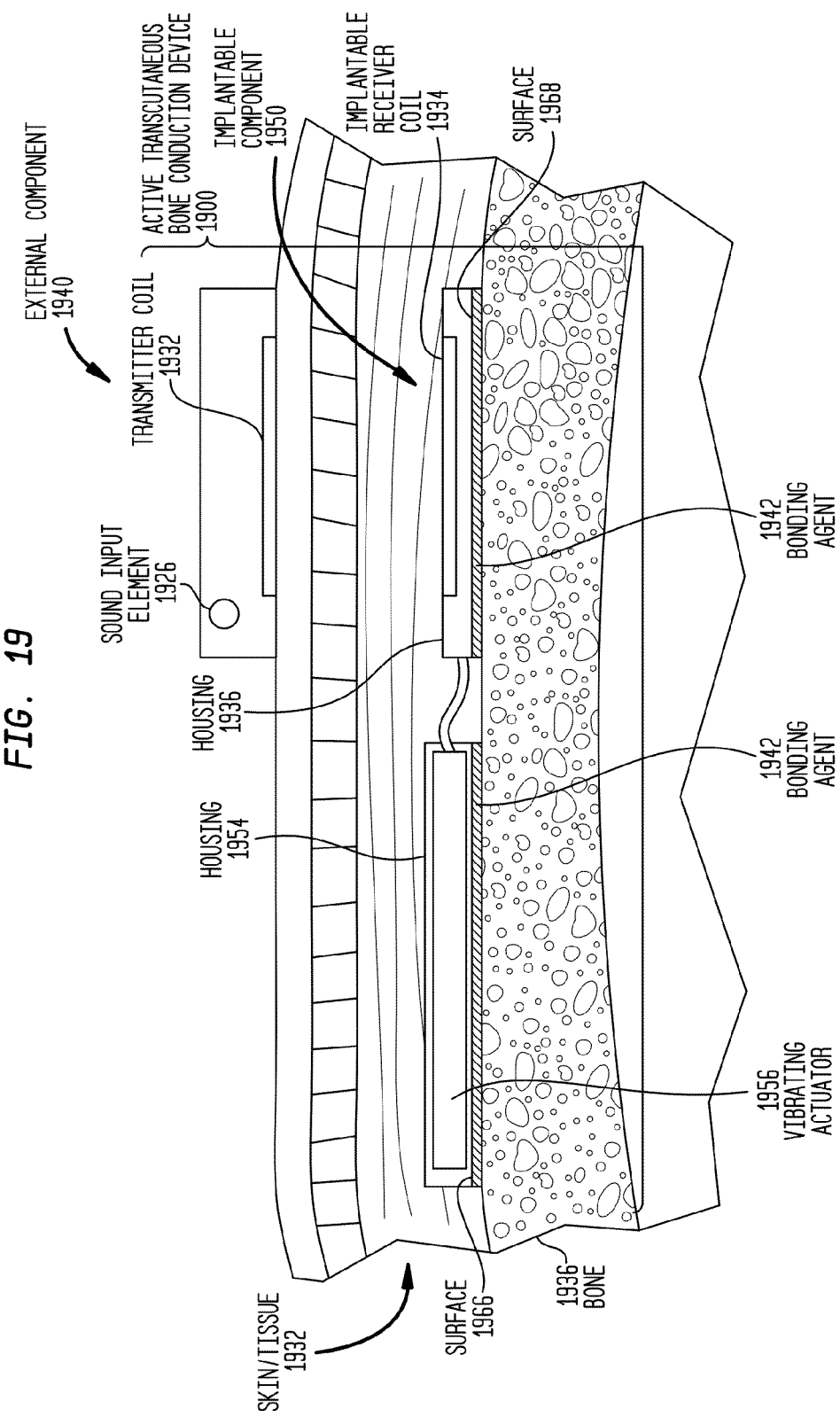
FIG. 19 is a schematic diagram illustrating an active transcutaneous bone conduction having one or more portions configured to be secured to a recipient with a bonding agent, in accordance with embodiments of the present invention.
Figure 20:
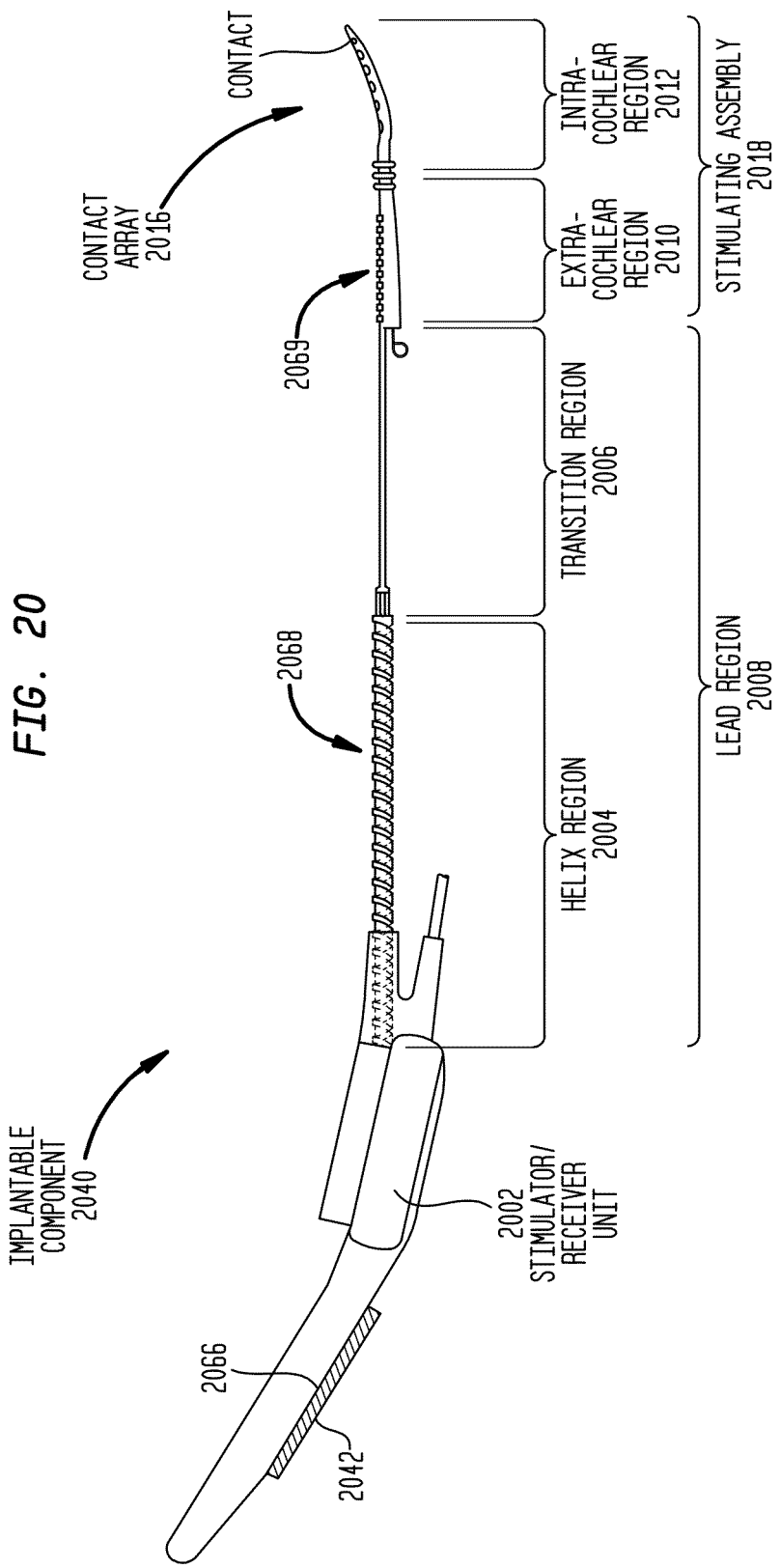
FIG. 20 is a schematic diagram illustrating an implantable component of a cochlear implant system having one or more portions configured to be secured to a recipient with a bonding agent, in accordance with embodiments of the present invention.

FIGS. 19 and 20 illustrate several implantable components having surfaces configured to be secured to a recipient with a bonding agent in accordance with embodiments of the present invention. More particularly, FIG. 19 illustrates an exemplary transcutaneous bone conduction device 1900 that includes an external device 1940 and an implantable component 1950 implanted beneath a recipient's skin/tissue 1932. The transcutaneous bone conduction device 1900 of FIG. 19 is an active transcutaneous bone conduction device because a vibrating actuator 1956 is located in a housing 1954 of the implantable component 1950. Similar to the actuator 256 of the embodiments of FIG. 1, the actuator 1956 is a device that converts electrical signals into vibration.

External component 1940 includes a sound input element 1926 that converts sound into electrical signals. These electrical signals are provided, via a transcutaneous magnetic inductance link, to vibrating actuator 1956 or to a sound processor (not shown) that processes the electrical signals. More specifically, a transmitter coil 1932 in the external component 1940 transmits the signals to implanted receiver coil 1934 located in housing 1936 of the implantable component 1950. Components (not shown) in one of the housings 1936 or 1954, such as, for example, a signal generator or an implanted sound processor, then generate electrical signals to be delivered to the actuator 1956. The actuator 1956 converts the electrical signals into vibration for delivery to the recipient's cochlea via bone 1936.

The actuator 1956 is mechanically coupled to the housing 1954. Housing 1954 and vibrating actuator 1956 collectively form a vibrating element. The housing 1954 has a surface 1966 that is configured to be substantially rigidly secured to bone 1936 with a bonding agent 1942. Similarly, housing 1936 has a surface 1968 configured to be secured to bone 1936 with a bonding agent 1942. It is to be appreciated that the surfaces 1966 and 1968 may be configured to facilitate attachment of the bonding agent 1942 to the surfaces (i.e., shapes, surface features, etc.). In certain embodiments, the surfaces 1966 and 1968 may have any of the surface features described with reference to FIGS. 4A-8B or other surface features configured to facilitate attachment of the bonding agent to the surfaces.

FIG. 20 is a simplified side view of an implantable component 2040 of a cochlear implant system having one or more portions configured to be secured to a recipient with a bonding agent. As shown, implantable component 2040 comprises a stimulator/receiver unit 2002 which receives encoded signals from an external component (not shown) of the cochlear implant system Implantable component 2040 terminates in a stimulating assembly 2018 that comprises an extra-cochlear region 2010 and an intracochlear region 2012. Intra-cochlear region 2012 is configured to be implanted in the recipient's cochlea and has disposed thereon a contact array 2016. In the present example, contact array 2016 comprises a plurality of contacts 2020 that may be electrical and/or optical contacts. Present commercial devices offered by the industry use electrical contacts, but research on the potential uses of optical stimulation alone of in conjunction with electrical or other stimulation mechanisms is ongoing.

Implantable component 2040 further comprises a lead region 2008 coupling stimulator/receiver unit 2002 to stimulating assembly 2018. Lead region 2008 comprises a region 2004 which is commonly referred to as a helix region, however, the required property is that the lead accommodate movement and is flexible, it does not need to be formed from wire wound helically. Lead region 2008 also comprises a transition region 2006 which connects helix region 2004 to stimulating assembly 2018. Helix region 2004 prevents lead region 2008 and its connection to stimulator/receiver 2002 and stimulating assembly 2018 from being damaged due to movement of implantable component 2040 (or part of 2040) which may occur, for example, during mastication.

It should be appreciated that implantable component 2040 is configured to be implanted in a recipient for an extended period of time. Additionally, all or portions of implantable component 2040 may be configured to be permanently implanted in the recipient. As such, in embodiments of the present invention implantable component 2040 includes one or more surfaces that are configured to be secured to the recipient with a bonding agent 2042. For example, in one embodiment stimulator/receiver unit 2002 has a surface 2066 configured to be secured to the recipient with the bonding agent 2042. In other embodiments, surfaces or portions 2068 of helix region and/or surfaces or portions 2069 of extra-cochlear region 2010 may be configured to be secured to the recipient with the bonding agent 2042.

Other implantable components that may be configured to be secured to a recipient's bone with a bonding agent include, but are not limited to, percutaneous bone anchors or implantable components of: direct acoustic stimulators, pacemakers, defibrillators, other functional electrical stimulation devices, etc.

FIG. 21 is a flowchart of a method 2100 in accordance with embodiments of the present invention. Method 2100 begins at step 2102 where an implantable component having a surface configured to be secured to a recipient is positioned at a selected location in the recipient. For example, the surface of the implantable component may be positioned adjacent to a bone of the recipient. At step 2104, the surface of the implantable component is secured to the recipient with a bonding agent.

In certain embodiments, securing the surface of the implantable component to the recipient with the bonding agent comprises applying the bonding agent to the surface of the implantable component, and pressing the surface of the implantable component to the recipient for a period of time. In accordance with other embodiments, the bonding agent is applied to a surface of the recipient's bone or other tissue and the surface of the implantable component is pressed to the bonding agent for a period of time to secure the implantable component.

In certain embodiments of FIG. 21, the surface of the implantable component includes surface features configured to facilitate attachment of the bonding agent to the surface. As such, the method 2100 of FIG. 21 may further comprise applying the bonding agent to the surface features.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A bone conduction device, comprising:
    an external component comprising:
        a sound input element configured to convert received sound into electrical signals,
        a sound processor configured to utilize the electrical signals to generate control signals,
        an actuator configured to generate mechanical vibration in response to the control signals received from the sound processor, and
        an external magnet mechanically coupled to the actuator; and an implantable anchor configured to be implanted adjacent to bone comprising:
a housing having a first surface configured to be secured to the bone with a bonding agent, wherein the first surface comprises one or more surface features having a shape such that the bonding agent is configured to undergo one or more turns when the bonding agent fills a plurality of the surface features so as to create an interlock between the bonding agent and the first surface, and
an implantable magnet enclosed in the housing configured to be magnetically coupled to the external magnet.

2. The bone conduction device of claim 1, wherein the surface features comprise pores in the first surface having an irregular shape so as to cause the bonding agent to undergo one or more turns when the bonding agent fills the pores.

3. The bone conduction device of claim 2, wherein the pores having irregular shapes are chemically etched pores.

4. The bone conduction device of claim 1, wherein the surface features comprise a plurality of elongate grooves each having an undercut region.

5. The bone conduction device of claim 4, wherein the plurality of elongate grooves comprise a plurality of L-shaped grooves.

6. The bone conduction device of claim 1, wherein the housing has a shape configured to distribute pressure resulting from the magnetic coupling and the vibration received from the external actuator.

7. The bone conduction device of claim 6, wherein the housing has a generally flattened-elliptical cross-sectional shape.

8. The bone conduction device of claim 6, wherein the housing has a generally semi-circular cross-sectional shape.

9. The bone conduction device of claim 6, wherein the housing has a generally hexagonal cross-sectional shape.

10. The bone conduction device of claim 6, wherein the housing has a generally rounded-cylindrical cross-sectional shape.

11. The bone conduction device of claim 1, wherein the implantable anchor comprises a plurality of implantable anchors each comprising:
a housing having a first surface configured to be secured to the bone with a bonding agent, wherein the first surface of each housing comprises one or more surface features having a shape such that the bonding agent is configured to undergo one or more turns when the bonding agent fills a plurality of the surface features so as to create an interlock between the bonding agent and the first surfaces of each housing, and
an implantable magnet enclosed in the housing configured to be magnetically coupled to the external magnet.

12. The bone conduction device of claim 11, wherein the plurality of implantable anchors are disposed on a support structure.

13. The bone conduction device of claim 12, wherein the support structure has a support surface comprising one or more surface features having a shape such that the bonding agent is configured to undergo one or more turns when the bonding agent fills a plurality of the surface features so as to create an interlock between the bonding agent and the support surface.

14. The bone conduction device of claim 12, wherein the support structure is a mesh.

15. The bone conduction device of claim 14, wherein the mesh is flexible.

16. The bone conduction device of claim 14, wherein the mesh is configured to osseointegrate with the bone.

17. The bone conduction device of claim 11, wherein the plurality of implantable anchors comprises two or more groups of implantable anchors configured to be secured to the bone at different locations.

* * * * *